US010180385B2

(12) United States Patent
Fox et al.

(10) Patent No.: US 10,180,385 B2
(45) Date of Patent: Jan. 15, 2019

(54) MULTI-SPECTRAL FILTER PROFILING AND QUALITY CONTROL FOR FLOW CYTOMETRY

(71) Applicant: Bio-Rad Laboratories, Inc., Hercules, CA (US)

(72) Inventors: Daniel Nelson Fox, Bellvue, CO (US); Susan Hunter, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 93 days.

(21) Appl. No.: 15/234,852

(22) Filed: Aug. 11, 2016

(65) Prior Publication Data

US 2017/0045436 A1 Feb. 16, 2017

Related U.S. Application Data

(60) Provisional application No. 62/204,001, filed on Aug. 12, 2015.

(51) Int. Cl.
*G01N 15/10* (2006.01)
*G01N 15/14* (2006.01)
*G01N 15/00* (2006.01)

(52) U.S. Cl.
CPC ..... *G01N 15/1012* (2013.01); *G01N 15/1434* (2013.01); *G01N 15/1459* (2013.01); *G01N 2015/0065* (2013.01); *G01N 2015/1006* (2013.01)

(58) Field of Classification Search
None
See application file for complete search history.

(56) References Cited

U.S. PATENT DOCUMENTS 7,123,795 B2 * 10/2006 Savard ............... G02B 6/02152
385/37
7,435,602 B2 * 10/2008 Gunstream .......... G01N 21/253
422/67

(Continued)

FOREIGN PATENT DOCUMENTS

WO   WO 2014/118326   10/2014
WO   WO 2015/084676   6/2015

OTHER PUBLICATIONS

WO 2014/118326 Ventana et al, Oct. 2014.*

(Continued)

*Primary Examiner* — Shawn Decenzo
*Assistant Examiner* — Jarreas C Underwood
(74) *Attorney, Agent, or Firm* — Weaver Austin Villeneuve & Sampson LLP

(57) ABSTRACT

Disclosed is a system and method for characterizing optical filters in a flow cytometer and optionally checking the operation of detectors in the flow cytometer. In some embodiments, the system may utilize an LED board having an opening through which the fluorescence and side scatter beams, rays, or images pass and light emitting diodes around the opening that emit light having different spectral profiles. The different spectral profiles allow the system to identify the optical filters that are placed in the flow cytometer, to verify detector operation, to assist in instrumentation troubleshooting, and to provide a quantitative reference for detector comparison.

26 Claims, 14 Drawing Sheets

(56) References Cited

U.S. PATENT DOCUMENTS

| | | | | |
|---|---|---|---|---|
| 7,990,525 B2* | 8/2011 | Kanda | .................... | G01N 21/51 |
| | | | | 356/73 |
| 8,084,260 B2* | 12/2011 | Gunstream | .......... | G01N 21/278 |
| | | | | 422/63 |
| 8,858,692 B2* | 10/2014 | Dwyer | .................... | A62B 7/10 |
| | | | | 128/205.29 |
| 9,551,616 B2* | 1/2017 | McQuilkin | ........... | G01J 3/2803 |
| 2008/0283607 A1 | 11/2008 | Kotlarsky et al. | | |
| 2012/0019834 A1* | 1/2012 | Bornhop | ................ | G01N 21/45 |
| | | | | 356/517 |
| 2012/0123722 A1* | 5/2012 | Kakuta | .............. | G01N 15/1429 |
| | | | | 702/104 |
| 2015/0369664 A1* | 12/2015 | Garsha | .................... | G01J 3/10 |
| | | | | 356/402 |

OTHER PUBLICATIONS

WO 2015/084676 Iris et al, Jun. 2014.*
International Search Report and Written Opinion, International Application No. PCT/US2016/046616, dated Oct. 21, 2016.
International Preliminary Report on Patentability, International Application No. PCT/US2016/046616, dated Feb. 22, 2018.

* cited by examiner

Wavelengths / Spectral Profiles (702-720) / Magnitude

| | 702 | 704 | 706 | 708 | 710 | 712 | 714 | 716 | 718 | 720 |
|---|---|---|---|---|---|---|---|---|---|---|
| 400nm | 96 | 0 | 0 | 0 | 0 | 0 | 0 | 0 | 0 | 0 |
| 410nm | 70 | 1 | 0 | 0 | 0 | 0 | 0 | 0 | 0 | 0 |
| 420nm | 26 | 4 | 0 | 0 | 0 | 0 | 0 | 0 | 0 | 0 |
| 430nm | 14 | 14 | 0 | 0 | 0 | 0 | 0 | 0 | 0 | 0 |
| 440nm | 8 | 44 | 0 | 0 | 0 | 0 | 0 | 0 | 0 | 0 |
| 450nm | 5 | 98 | 0 | 0 | 0 | 0 | 0 | 0 | 0 | 0 |
| 460nm | 3 | 52 | 2 | 0 | 0 | 0 | 0 | 0 | 0 | 0 |
| 470nm | 1 | 20 | 7 | 1 | 0 | 0 | 0 | 0 | 0 | 0 |
| 480nm | 0 | 8 | 19 | 5 | 0 | 0 | 0 | 0 | 0 | 0 |
| 490nm | 0 | 2 | 50 | 10 | 0 | 0 | 0 | 0 | 0 | 0 |
| 500nm | 0 | 0 | 84 | 22 | 0 | 0 | 0 | 0 | 0 | 0 |
| 510nm | 0 | 0 | 90 | 50 | 0 | 0 | 0 | 0 | 0 | 0 |
| 520nm | 0 | 0 | 52 | 84 | 0 | 0 | 0 | 0 | 0 | 0 |
| 530nm | 0 | 0 | 30 | 97 | 0 | 0 | 0 | 0 | 0 | 0 |
| 540nm | 0 | 0 | 15 | 68 | 0 | 0 | 0 | 0 | 0 | 0 |
| 550nm | 0 | 0 | 8 | 44 | 0 | 0 | 0 | 0 | 0 | 0 |
| 560nm | 0 | 0 | 4 | 28 | 2 | 0 | 0 | 0 | 0 | 0 |
| 570nm | 0 | 0 | 1 | 17 | 9 | 0 | 0 | 0 | 0 | 0 |
| 580nm | 0 | 0 | 0 | 10 | 34 | 0 | 0 | 0 | 0 | 0 |
| 590nm | 0 | 0 | 0 | 5 | 100 | 1 | 0 | 0 | 0 | 0 |
| 600nm | 0 | 0 | 0 | 2 | 46 | 4 | 0 | 0 | 0 | 0 |
| 610nm | 0 | 0 | 0 | 1 | 15 | 15 | 0 | 0 | 0 | 0 |
| 620nm | 0 | 0 | 0 | 0 | 5 | 47 | 0 | 0 | 0 | 0 |
| 630nm | 0 | 0 | 0 | 0 | 2 | 100 | 0 | 0 | 0 | 0 |
| 640nm | 0 | 0 | 0 | 0 | 0 | 46 | 3 | 0 | 0 | 0 |
| 650nm | 0 | 0 | 0 | 0 | 0 | 16 | 10 | 0 | 0 | 0 |
| 660nm | 0 | 0 | 0 | 0 | 0 | 7 | 16 | 0 | 0 | 0 |
| 670nm | 0 | 0 | 0 | 0 | 0 | 3 | 66 | 0 | 0 | 0 |
| 680nm | 0 | 0 | 0 | 0 | 0 | 1 | 100 | 0 | 0 | 0 |
| 690nm | 0 | 0 | 0 | 0 | 0 | 0 | 68 | 0 | 0 | 0 |
| 700nm | 0 | 0 | 0 | 0 | 0 | 0 | 24 | 0 | 0 | 0 |
| 710nm | 0 | 0 | 0 | 0 | 0 | 0 | 7 | 0 | 0 | 0 |
| 720nm | 0 | 0 | 0 | 0 | 0 | 0 | 4 | 6 | 4 | 0 |
| 730nm | 0 | 0 | 0 | 0 | 0 | 0 | 0 | 100 | 7 | 0 |
| 740nm | 0 | 0 | 0 | 0 | 0 | 0 | 0 | 16 | 14 | 0 |
| 750nm | 0 | 0 | 0 | 0 | 0 | 0 | 0 | 1 | 34 | 0 |
| 760nm | 0 | 0 | 0 | 0 | 0 | 0 | 0 | 0 | 74 | 0 |
| 770nm | 0 | 0 | 0 | 0 | 0 | 0 | 0 | 0 | 100 | 0 |
| 780nm | 0 | 0 | 0 | 0 | 0 | 0 | 0 | 0 | 76 | 2 |
| 790nm | 0 | 0 | 0 | 0 | 0 | 0 | 0 | 0 | 36 | 4 |
| 800nm | 0 | 0 | 0 | 0 | 0 | 0 | 0 | 0 | 15 | 8 |
| 810nm | 0 | 0 | 0 | 0 | 0 | 0 | 0 | 0 | 8 | 16 |
| 820nm | 0 | 0 | 0 | 0 | 0 | 0 | 0 | 0 | 0 | 30 |
| 830nm | 0 | 0 | 0 | 0 | 0 | 0 | 0 | 0 | 0 | 50 |
| 840nm | 0 | 0 | 0 | 0 | 0 | 0 | 0 | 0 | 0 | 74 |
| 850nm | 0 | 0 | 0 | 0 | 0 | 0 | 0 | 0 | 0 | 90 |

Figure 8D

MULTI-SPECTRAL FILTER PROFILING AND QUALITY CONTROL FOR FLOW CYTOMETRY

CROSS REFERENCE TO RELATED APPLICATIONS

This application claims benefit of priority under 35 U.S.C. § 119(e) to U.S. Provisional Patent Application No. 62/204,001, filed Aug. 12, 2015 and titled "MULTI-SPECTRAL FILTER PROFILING AND QUALITY CONTROL FOR FLOW CYTOMETRY," which is hereby incorporated by reference herein in its entirety.

BACKGROUND

Flow cytometers have been used extensively for analyzing cells and various particles. As a diagnostic tool, flow cytometers have been very effective in providing detailed information regarding the physiology of cells and particles. Flow cytometers have been used for analysis of cells and other particles in both research laboratories and in clinics. Flow cytometers include traditional hydrodynamically focused sample streams in a cuvette, a hydrodynamically focused sample stream with a jet-in-air sorting flow cytometer, and microfluidic systems that do not use focusing. For purposes of this application, the term "flow cytometer" should include all of these different types of flow cytometers.

In many typical flow cytometers, particles or cells that are of interest may be tagged with a marker, e.g., a fluorescing indicator, that may be stimulated to provide a quantifiable response, e.g., to emit light that may be detected by optical sensors. For example, in a typical flow cytometry system, a sample may be mixed with a fluorescent indicator that is known to bind to particles of interest and, in doing so, become photoreactive to a particular wavelength or wavelengths of light. The sample may then be focused into a stream or other constrained area and illuminated with high-intensity light of that particular wavelength or wavelengths—any photo-reactive indicator that is present will then fluoresce in response to such illumination. Such indicators normally are selected to emit light of other wavelengths than the stimulating light. Light that is emitted from the stimulated indicator may then be captured and measured to provide an estimate of how much indicator was present and fluorescing, thereby allowing for quantification of the amount of particles to which the indicator is bound.

In practice, there are many hurdles to obtaining such a measurement. For example, the intensity of stimulating light that must be provided to the indicator in order to cause it to fluoresce at a detectable intensity level at the desired wavelength may be several orders of magnitude higher than the intensity with which the fluorescing light is emitted. Since the target cells and particles are typically quite small in size, the stimulating light may need to be tightly focused on the cells or particles in order to provide sufficient stimulating light intensity without needlessly increasing the energy expenditure needed to stimulate the indicator.

Furthermore, a fluorescing particle or cell may emit fluorescing light in a generally omnidirectional manner, thereby making it impractical to efficiently capture all of the light that is emitted via fluorescence. This reduces the amount of fluorescing light that may be captured and quantified, thereby further reducing the measurement efficiency of a flow cytometry system. Another issue that further complicates flow cytometry measurements is that the fluorescing light that is ultimately delivered to a detector system capable of measuring the intensity of such fluorescing light may be extremely faint—so faint that many photodetector systems will be unable to adequately quantify it. To that end, extremely sensitive photodetector systems may be used, such as photomultiplier tubes, which convert the received florescent light into an electrical current that may be amplified by multiple orders of magnitude, e.g., 100,000 times.

In order to allow for a single flow cytometer to be used to process multiple different types of particles or cells and indicators, either separately or concurrently, many flow cytometers may include multiple photodetector systems, each equipped with a filtering system that allows for the flow cytometer to be easily reconfigured by removing or exchanging the filters. This allows each photodetector to be tuned to be receptive to only a particular spectrum of light, thereby allowing each photodetector to be used to detect the presence of a different indicator (or the presence of a different spectrum of received light—in some cases, an indicator may emit multiple different frequencies of light, and multiple different photodetectors may be used to detect each separate frequency).

Discussed herein are techniques and systems that improve upon flow cytometer systems having such reconfigurable filtering systems.

SUMMARY

In some embodiments, a flow cytometry system may be provided that includes at least one sample illumination source is configured to deliver light to a corresponding sample location, thereby causing sample light to be emitted by or scattered off of particles in the corresponding sample location. The flow cytometry system may also include focusing optics that are configured to direct the sample light from each sample location along one or more optical paths such that each optical path passes through a corresponding one or more optical filter elements and terminates at a corresponding detector that is configured to produce output data indicative of the measured intensity of light reaching that detector. The flow cytometry system may also include a calibration light source that is configured to independently emit different spectral profiles of calibration light, each spectral profile of calibration light having one or more peaks at different wavelengths, such that the emitted calibration light is directed along at least a portion of each of the optical paths. The flow cytometry system may also include one or more processors and a memory that stores computer-executable instructions that, when executed by the one or more processors, cause the one or more processors to: receive the output data from each of the detectors responsive to that detector receiving calibration light from the calibration light source, and determine filtering characteristics for the optical filter elements along each optical path by analyzing the output data produced during the emission of at least two different spectral profiles of calibration light by the calibration light source.

In some such embodiments, the computer-executable instructions may further include instructions that, when executed by the one or more processors, cause the one or more processors to: cause the calibration light source to emit, at a first time, first calibration light having a first spectral profile; obtain first output data from each of the detectors responsive to the detectors receiving the first calibration light from the calibration light source at the first time; cause the calibration light source to emit, at a second time after the first time, second calibration light having the first spectral profile; obtain second output data from each of the detectors responsive to the detectors receiving the second calibration light from the calibration light source at the second time; and compare the second output data to the first output data to determine if there has been a change in optical performance of the flow cytometry system.

In some other or further such embodiments of the flow cytometry system, the one or more detectors may include a first detector, and the computer-executable instructions may further include instructions that, when executed by the one or more processors, cause the one or more processors to: obtain first output data from the first detector produced in response to detection by the first detector of first calibration light having a first spectral profile; obtain second output data from the first detector produced in response to detection by the first detector of second calibration light having a second spectral profile that is different from the first spectral profile; compare the first output data and the second output data against a database of spectral fingerprints, each spectral fingerprint associated with a particular filtering characteristic and having a first component associated with the first spectral profile and a second component associated with the second spectral profile; and determine the filtering characteristics for the optical filter elements along the optical path corresponding to the first detector by identifying the particular filtering characteristic by, at least in part, correlating the first output data and the second output data with the first component and the second component, respectively.

In some other or further such embodiments of the flow cytometry system, the one or more detectors may include a first detector, and the computer-executable instructions may further include instructions that, when executed by the one or more processors, cause the one or more processors to: obtain first output data from the first detector produced in response to detection by the first detector of first calibration light having a first spectral profile; compare the first output data against a database of spectral fingerprints, each spectral fingerprint associated with a particular filtering characteristic and having a first component associated with the first spectral profile; and determine the filtering characteristics for the optical filter elements along the optical path corresponding to the first detector by identifying the particular filtering characteristic by, at least in part, correlating the first output data with the first component, respectively.

In some other or further such embodiments of the flow cytometry system, the one or more detectors may include a first detector, and the computer-executable instructions may further include instructions that, when executed by the one or more processors, cause the one or more processors to: obtain first output data from the first detector produced in response to detection by the first detector of first calibration light having a first spectral profile; obtain second output data from the first detector produced in response to detection by the first detector of second calibration light having a second spectral profile that is different from the first spectral profile and that also overlaps with the first spectral profile; compare the first output data and the second output data by determining a ratio of the second output data to the first output data; and determine the filtering characteristics for the optical filter elements along the optical path corresponding to the first detector by, at least in part, comparing the ratio against intensity ratios of the first spectral profile and the second spectral profile corresponding with a plurality of wavelengths.

In some such embodiments of the flow cytometry system, the computer-executable instructions may further include instructions that, when executed by the one or more processors, cause the one or more processors to obtain additional output data from the first detector produced in response to detection by the first detector of one or more additional emissions of calibration light having spectral profiles other than the first spectral profile and the second spectral profile and determine that none of the additional output data indicates any detection of the additional emissions of calibration light by the first detector.

In some embodiments of the flow cytometry system, the computer-executable instructions may further include instructions that, when executed by the one or more processors, cause the one or more processors to: compare the filtering characteristics for the optical filter elements along the optical path with predefined filtering characteristics associated with that optical path and provide an indication via a user interface as to whether the filtering characteristics for the optical filter elements along the optical path are within a threshold amount of the predefined filtering characteristics associated with that optical path.

In some embodiments of the flow cytometry system, a different subset of the one or more optical paths may pass through each optical filter element.

In some embodiments of the flow cytometry system, each of the one or more optical paths may be defined, at least in part, by an optical fiber.

In some such embodiments of the flow cytometry system, the focusing optics may include objective optics configured to focus the sample light and the calibration light onto the ends of the one or more optical fibers.

In some embodiments of the flow cytometry system, each of the one or more optical paths may pass through a pinhole aperture.

In some embodiments of the flow cytometry system, the calibration light source may include a printed circuit board having an opening through it and a plurality of light emitting diodes (LEDs) placed around the periphery of the opening. In such embodiments, the plurality of LEDs may be configured to emit the calibration light and the one or more optical paths may pass through the opening.

In some embodiments of the flow cytometry system, the calibration light source may be configured to emit calibration light that is directed through the sample location and into the focusing optics.

In some embodiments, a method is provided for determining filtering characteristics for a plurality of optical filter elements in a flow cytometry system. In such a flow cytometry system, a different subset of a plurality of optical paths may pass through each of the optical filter elements, and each optical path may direct emitted or scattered sample light from a sample location to a corresponding detector. The method may include: emitting different spectral profiles of calibration light from a calibration light source, wherein each spectral profile of calibration light has one or more intensity peaks at different wavelengths; directing some of the calibration light along at least a portion of each of the optical paths; measuring, for each different spectral profile of calibration light, the light intensity at each of the detectors, wherein each of the detectors produces output data that is indicative of the measured light intensity of the calibration light that reaches the detector; and analyzing the output data from one of the detectors produced during the emission of at least two different spectral profiles of calibration light by the calibration light source to determine the filtering characteristics of the optical filter elements along the optical path corresponding to that detector.

In some embodiments of the method, the method may further include: causing the calibration light source to emit, at a first time, first calibration light having a first spectral profile; obtaining first output data from each of the detectors responsive to the detectors receiving the first calibration light from the calibration light source at the first time; causing the calibration light source to emit, at a second time after the first time, second calibration light having the first spectral profile; obtaining second output data from each of the detectors responsive to the detectors receiving the second calibration light from the calibration light source at the second time; and comparing the second output data to the first output data to determine if there has been a change in optical performance of the flow cytometry system In some other or additional embodiments of the method, the method may further include: obtaining first output data from a first detector of the one or more detectors produced in response to detection by the first detector of first calibration light having a first spectral profile; obtaining second output data from the first detector produced in response to detection by the first detector of second calibration light having a second spectral profile that is different from the first spectral profile; comparing the first output data and the second output data against a database of spectral fingerprints, each spectral fingerprint associated with a particular filtering characteristic and having a first component associated with the first spectral profile and a second component associated with the second spectral profile; and determining the filtering characteristics for the optical filter elements along the optical path corresponding to the first detector by identifying the particular filtering characteristic by, at least in part, correlating the first output data and the second output data with the first component and the second component, respectively.

In some other or additional embodiments of the method, the method may further include: obtaining first output data from a first detector of the one or more detectors produced in response to detection by the first detector of first calibration light having a first spectral profile; comparing the first output data against a database of spectral fingerprints, each spectral fingerprint associated with a particular filtering characteristic and having a first component associated with the first spectral profile; and determining the filtering characteristics for the optical filter elements along the optical path corresponding to the first detector by identifying the particular filtering characteristic by, at least in part, correlating the first output data with the first component, respectively.

In some other or additional embodiments of the method, the method may further include: obtaining first output data from a first detector of the detectors responsive to detection by the first detector of first calibration light having a first spectral profile; obtaining second output data from the first detector responsive to detection by the first detector of second calibration light having a second spectral profile that is different from the first spectral profile and that also overlaps with the first spectral profile; comparing the first output data and the second output data by determining a ratio of the second output data to the first output data; and determining the filtering characteristics for the optical filter elements along the optical path corresponding to the first detector by comparing the ratio against intensity ratios of the first spectral profile and the second spectral profile corresponding with a plurality of wavelengths.

In some other or additional embodiments of the method, the method may further include: obtaining additional output data from the first detector responsive to detection by the first detector of one or more additional emissions of calibration light having spectral profiles other than the first spectral profile and the second spectral profile and determining that none of the additional output data indicates any detection of the additional emissions of calibration light by the first detector.

BRIEF DESCRIPTION OF THE DRAWINGS

FIG. 8D is a table of spectral fingerprints using the LED spectral profiles of FIG. 7A.

DETAILED DESCRIPTION OF THE EMBODIMENTS

Figure 1:
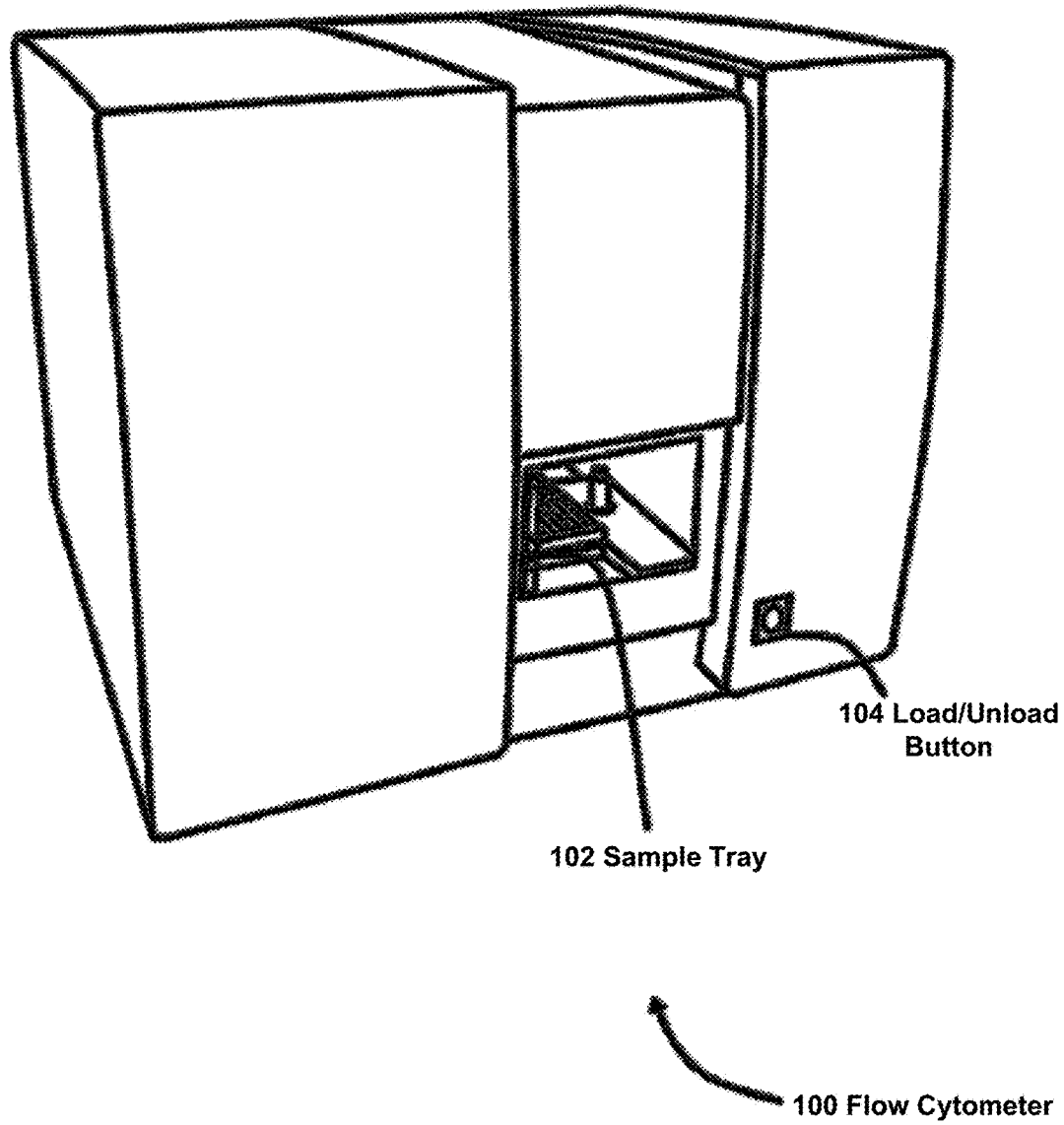
FIG. 1 is a perspective view of an example embodiment of a flow cytometer.

FIG. 1 is a depiction of an embodiment of a flow cytometer in accordance with the present invention. As shown, the flow cytometer 100 is a self-contained unit that can easily fit on a desk top. As illustrated in FIG. 1, the flow cytometer 100 has a load/unload button 104 to extend and retract the sample tray 102, which allows the insertion of samples to be tested by the flow cytometer 100.

Figure 2:
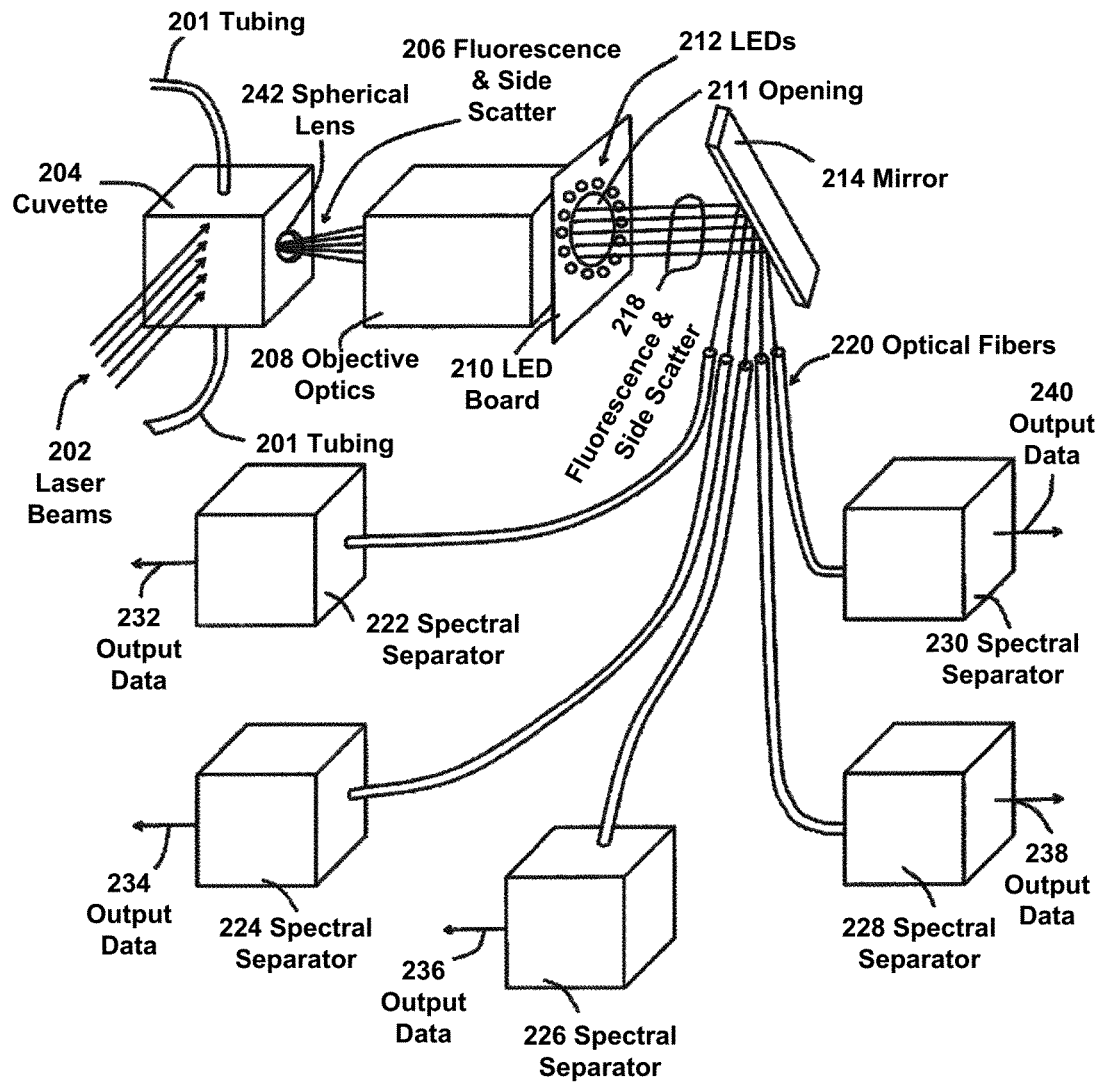
FIG. 2 is a schematic block diagram illustrating the operation of a portion of the example embodiment of the flow cytometer illustrated in FIG. 1.

FIG. 2 is a schematic block diagram of an example optical layout of the detector portion of the embodiment of the flow cytometer illustrated in FIG. 1. As shown in FIG. 2, the optical layout 200 includes a cuvette 204, objective optics 208, an LED board 210, a series of optical fibers 220 and spectral separators 222, 224, 226, 228, 230. The cuvette 204 has tubing 201 that causes the cells or particles (in this application, the term "particles" is to be understood as referring to particles, cells, or other microscopic item) that are to be interrogated to flow through an interior portion of the cuvette 204; this sample fluid flow may also undergo hydrodynamic focusing to concentrate the particles that are to be interrogated into one or more sample locations. For example, hydrodynamic focusing may concentrate the sample towards the centerline of the cuvette or the sample may be flowed through a small-diameter tube. In such embodiments, the one or more sample locations may be arrayed along the centerline or along the centerline of the tube. As the sample flows through the one or more sample locations, light from one or more sample illumination sources may be used to illuminate or interrogate the sample. For example, laser beams 202 may be projected onto the sample locations, e.g., into the cuvette 204, and thereby illuminate or interrogate the particles that are delivered to the sample locations via the tubing 201. The particles in the sample may be marked with various markers that are attached to fluorochromes; these fluorochromes, when illuminated by the light from the one or more sample illumination sources, may fluoresce at particular wavelengths of light. Some of the sample illumination light may also scatter off of the particles as well. The light that is emitted by the fluorochromes attached to the particles in response to being interrogated or illuminated by the one or more sample illumination sources and the sample illumination light that is scattered off of the particles are collectively referred to herein as "sample light."

The flow cytometer may include various optical components, such as a spherical lens 242 and objective optics 208, that may collect sample light from the one or more sample locations and may then direct the collected sample light along one or more optical paths, such as optical fibers 220. In a typical arrangement, the one or more sample illumination sources may be oriented such that the sample illumination light primarily travels along a path that is orthogonal to the direction that the sample light that reaches the optical components may follow. This may prevent the sample illumination light from having a direct path to the optical components and the optical paths, thereby helping ensure that the light that is collected by the optical components is only the sample light. It is to be understood that the one or more sample illumination sources may generally be narrow-band light sources, e.g., lasers or single-color LEDs, that emit light in wavelengths that are different from the wavelengths of light that the fluorochromes may emit in response to being illuminated with the sample illumination light. This allows sample light arising from fluorescence of the fluorochrome to be differentiated from sample light arising from scattered sample illumination light, thereby improving the accuracy and capabilities of the flow cytometry system. For example, scattered light in the sample light may be analyzed to gain insight as to the shape or overall size of the particle, whereas fluorescent light in the sample light may allow for identification of particular types of particle.

As noted above, the sample light may be directed along one or more optical paths. Each optical path may convey the sample light (or a portion of it) to a different detector; thus, each detector may have its own unique optical path that terminates at that detector. In some embodiments, a plurality of optical paths may share some common components. For example, in the optical layout 200, each optical fiber 220 leads to a separate spectral separator 222, 224, 226, 228, or 230. Each of these spectral separators may have a collection of filters and/or dichroic mirrors within it that subdivides the sample light travelling along each of the optical fibers 220 into multiple branches, and each such branch may terminate at a separate detector within the spectral separators. Thus, the optical fiber 220 leading to a particular spectral separator may be viewed as being a common element of the multiple optical paths that terminate at the detectors within that spectral separator.

Of course, there are other methods and ways of transmitting the light to the spectral separators other than using optical fibers 220. For example, in some flow cytometers, a pinhole strip is used with prisms to bend light from the different pinholes to different filter/photomultiplier tube pairs in free space. This alternative approach is simpler in some respects, but may be more complex in other respects. For example, the alternative approach may require a much larger space to implement, making such units bulkier. Additionally, other types of optical elements may be used in place of the prism. The term "optical element," as used herein, is to be understood to refer to a prism, mirror, lens, or other optical device that can direct light. Generically, the use of optical fibers or the free space propagation technique can be generically be referred to as a process for channeling light to spectral detectors or light channeling devices. Generally speaking, the sample light may be focused on some sort of an optical receiving port or element, e.g., the end of an optical fiber, a pinhole aperture, etc., which may serve to introduce the sample light to an optical transmission system, e.g., an optical fiber, a prismatic or mirror-based optical system, etc., that conveys the sample light to one or more detectors.

The purpose of the flow cytometer 100 is to identify particular characteristics of the particles that are being interrogated. As noted earlier, fluorochromes that are attached to markers fluoresce when interrogated by sample illumination sources, e.g., lasers, having specific frequencies. Multiple markers and multiple fluorochromes may be used to identify different aspects of the cells. In immunology, the markers may include antibodies that bond to specific antigens on the cells. For example, a fluorochrome may be attached to a specific antibody that is selected to bond to a particular antigen on a cell. Interrogation by a laser causes the fluorochrome that is attached to the antibody to fluoresce, which identifies the antigen that is present on the cell. The amount of fluorescence measured by the flow cytometer is an indication of the number of antigens that are present on the cell. Numerous different markers and fluorochromes can be used, and various wavelengths of lasers can cause fluorescence at a number of other different wavelengths. For example, the use of a 405 nanometer laser as a sample illumination source may cause seven different fluorescent responses, each from a different marker on or inside a particle, which may be filtered and individually detected by a corresponding seven different filters and seven different photomultiplier tubes. Typically these filters are optical bandpass filters, and it may be common in some embodiments for the sample light that is delivered to each such detector to be filtered multiple times, with some of these filters simultaneously filtering light delivered to different detectors. In addition, side scatter may also occur when the laser interrogates the particles. The side scatter constitutes scattered light indicative of the morphology of the particle.

Referring again to FIG. 2, the sample light, which is composed of fluorescence and side scatter 206, is emitted from the cuvette 204 through a spherical cuvette lens 242 into objective optics 208, which may be collectively referred to herein as "focusing optics." The objective optics 208 may be configured to focus the fluorescence and side scatter 206, i.e., sample light, onto the ends of the optical fibers 220, e.g., by reflecting the sample light off of a mirror 214. The optical fibers 220 may then convey the sample light to the spectral separators for detection and analysis. In the depicted embodiment, and as discussed in more detail below with respect to FIG. 4, the spectral separators 222, 224, 226, 228, and 230 may each have a number of dichroic mirrors, i.e., beam-splitting mirrors that direct light of one spectral profile along one direction while directing light of a different spectral profile along a different direction, and/or optical filter elements that are arranged so as to allow the sample light that reaches each detector within each spectral separator to be differently filtered. For the purposes of this disclosure, the term "optical filter element" is to be understood to refer to both optical filters, i.e., media that only permit light of particular spectral profiles to pass through, and dichroic mirrors, i.e., media that are optically transparent to light of one spectral profile and optically reflective to light of a different spectral profile. Examples of some common optical filter elements that may be used in a flow cytometry system include optical bandpass filters such as an optical bandpass filter having a center wavelength of 525 nm and a bandwidth (also referred to as the "full-width at half maximum" or "FWHM" of the filter) of 35 nm, an optical bandpass filter having a center wavelength of 575 nm and a bandwidth of 15 nm, an optical bandpass filter having a center wavelength of 670 nm and a bandwidth of 30 nm, and an optical longpass filter with a cut-on wavelength of 750 nm at 50% of peak transmission. It is to be understood that these example filters are merely representative examples of various filters that may be used, and that a large number of other filters having other filtering characteristics may also be utilized in a flow cytometry system. It is also to be understood that other specific types of focusing optics may be used in place of the spherical cuvette lens 242 and the objective optics 208, as well as the other components discussed above, in order to provide the functionality of the focusing optics, i.e., in order to direct the sample light along the optical paths that the sample light follows on its way to the detectors.

In systems like the embodiment that is depicted, one or more of the optical filter elements along each optical path may be swappable or reconfigurable, thereby allowing the overall filtering characteristics for each optical path to be user-adjustable. This allows the flow cytometer to be easily reconfigured to work with different markers and different sample illumination sources, if desired. However, the present inventors also realized that a user-reconfigurable optical filtering system may be inadvertently mis-configured, e.g., by placing the wrong optical filter element in the wrong optical filter element location. This may have the effect of inadvertently screening out the sample light that is of interest from a particular detector, thereby causing a false negative. Alternatively, sample light that is to be filtered out may inadvertently be allowed to pass through and reach the detector, thereby generating false positives. The present inventors conceived of a filter testing and validation system that may be implemented in such reconfigurable filter element systems to prevent such errors.

Such a filter testing and validation system may utilize a calibration light source, which may be configured to independently emit calibration light of different spectral profiles such that the emitted calibration light is directed along at least a portion of each of the optical paths along which the sample light is directed. In the system of FIG. 2, for example, the calibration light source takes the form of an LED board 210, which has an opening through the it that allows the optical paths (and the sample light directed along the optical paths) to pass through the LED board 210. Thus, the fluorescence and side scatter 218 that may be emitted from the objective optics 208 may travel through the opening 211 in the LED board 210 and be reflected by mirror 214 onto the ends of the optical fibers 220. The LED board 210 may contain a number of LEDs that generate light having different spectral profiles, e.g., one or more LEDs in the number of LEDs may generate light predominantly in the green spectrum, whereas another one or more LEDs in the number of LEDs may generate light predominantly in the red spectrum. Generally speaking, the LEDs (or other light-emitting devices) in the calibration light source may have relatively narrow bandwidths, e.g., in the 100 nm to 150 nm range, with clearly pronounced peak wavelengths. An example spectrum of different peak frequencies and bandwidths of LEDs in an example calibration light source is illustrated, in accordance with one embodiment, in FIG. 8A. As can be seen, 10 different spectral profiles 702, 704, 706, 708, 710, 712, 714, 716, 718, and 720 are shown. Each spectral profile has a clearly pronounced peak and a bandwidth of on the order of approximately 100 nm to 150 nm. For example, the spectral profile 702 is representative of an LED that emits light predominantly in the violet spectrum, the spectral profiles 704 and 706 are representative of LEDs that emit light predominantly at opposing ends of the blue spectrum, the spectral profile 708 is representative of an LED that emits light predominantly in the green spectrum, the spectral profile 710 is representative of an LED that emits light predominantly in the yellow-orange spectrum, the spectral profiles 712, 714, and 716 are representative of LEDs that emit light predominantly in the red spectrum, and the spectral profiles 718 and 720 are representative of LEDs that emit light predominantly in the infrared spectrum. The LEDs associated with each of these ten spectral profiles may be illuminated separately, thereby allowing calibration light to be emitted that corresponds with each separate spectral profile to be emitted in isolation. In some embodiments, LEDs for subsets of the spectral profiles may be illuminated simultaneously, e.g., the LEDs that produce the spectral profiles 702 and 704 may be illuminated simultaneously to produce calibration light having a spectral profile that is a combination of the spectral profiles 702 and 704 (in such cases, the combined spectral profile will be differently shaped, as the overlapping portions of the spectral profiles may be additively combined).

Thus, in the depicted example embodiment of FIG. 2, each of the LEDs 212 may generate a narrow-band optical signal that is also reflected by mirror 214 onto the openings of the optical fibers 220, thereby causing the emitted calibration light to be directed along at least a portion of the optical paths that the sample light follows. The purpose of the LEDs 212 is to check and verify the operation of the spectral separators 222, 224, 226, 228, 230. The LEDs 212 can be flashed individually, or together, in order to check the operation of the spectral separators 222-230. Each of the spectral separators 222-230 creates output data 232, 234, 236, 238, 240. Since each of the LEDs 212 have specific frequency bands that are separate optical frequencies, the spectral separators 222-230 can be checked and verified, as discussed in more detail below.

Figure 3:
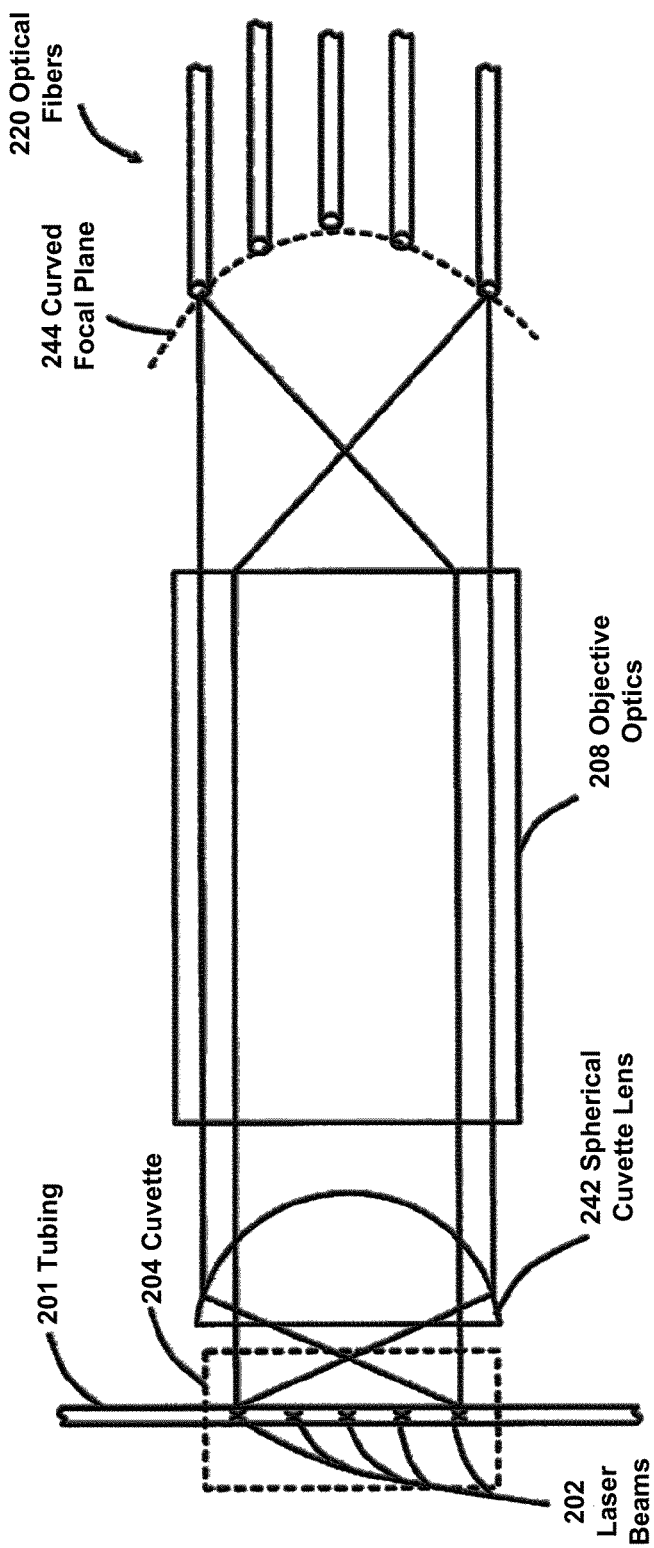
FIG. 3 is a schematic illustration of the focusing, in one embodiment, of the side scatter and fluorescence from the particles onto the optical fibers using a cuvette lens and objective lenses.

FIG. 3 is a schematic side diagram that illustrates the focusing of the fluorescence and side scatter on the ends of the optical fibers 220. As illustrated in FIG. 3, laser beams 202 interrogate the particles in the sample (each location where a laser beam traverses the sample pathway, e.g., the cuvette, may be thought of as a "sample location") that is in the cuvette 204 and that is delivered to the cuvette 204 via the tubing 201 (it is to be understood that the tubing 201 does not pass through the cuvette, but that separate pieces of tubing 201 are attached to either end of the cuvette; the cuvette itself may be an optically transparent vessel that constrains the sample to a particular location for illumination by the sample light source). The fluorescence and side scatter light that is emitted from the particles at each sample location in response to the laser interrogation is collected by the spherical cuvette lens 242. The spherical cuvette lens 242, together with the objective optics 208, focuses the fluorescence and side scatter light on the ends of the optical fibers 220. The focus points, in this example, are located on a curved focal plane 244, as illustrated by the location of the openings of the optical fibers 220. Of course, other optical configurations may be used as well, depending on the particular configuration of a flow cytometer.

Figure 4:
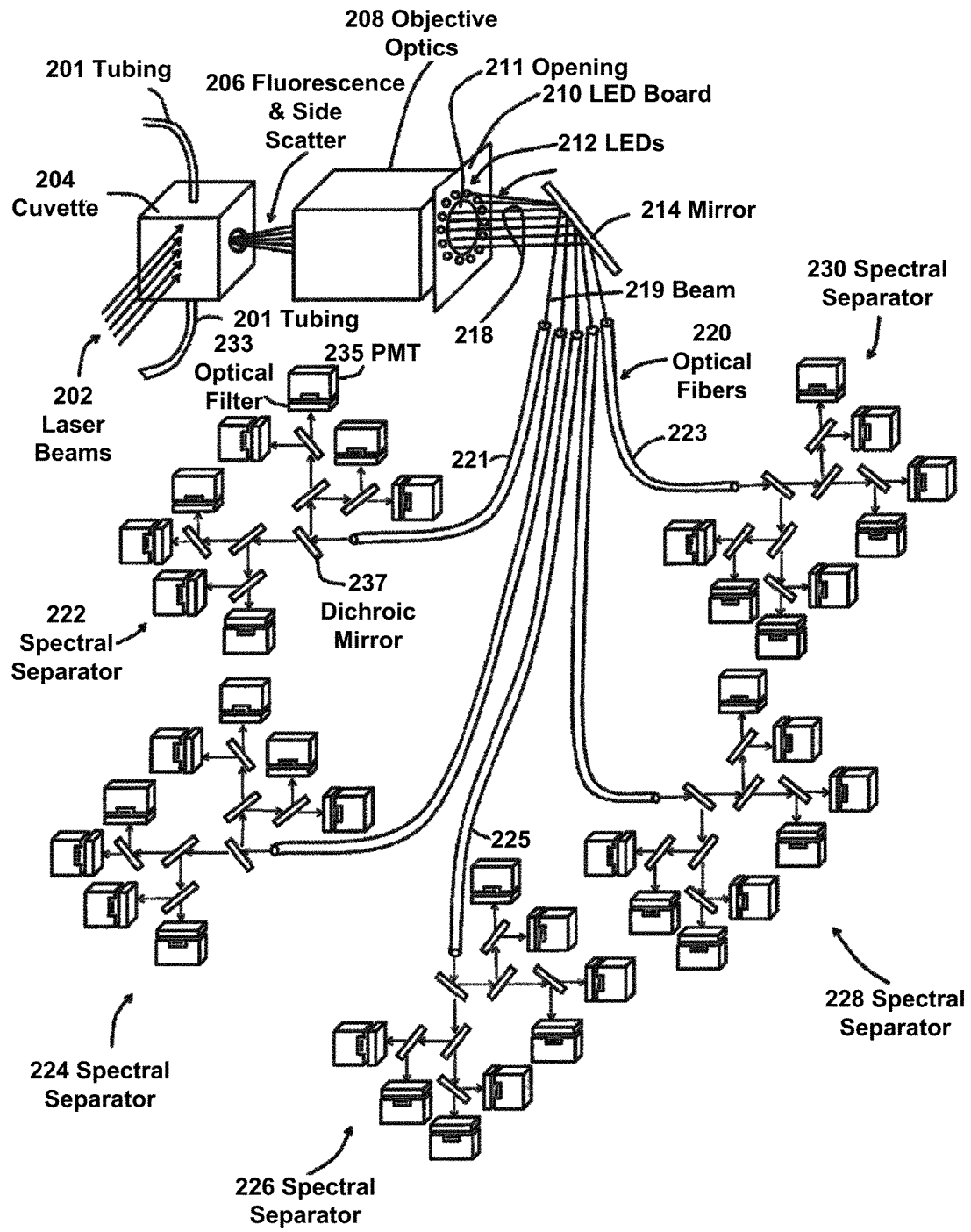
FIG. 4 is another block diagram illustrating a portion of the operation of the example embodiment of the flow cytometer of FIG. 1.

FIG. 4 is a more detailed view of the embodiment illustrated in FIG. 2. In accordance with FIG. 4, the laser beams 202 enter the cuvette 204 and interrogate the particles that are delivered via the tubing 201. The fluorescence and side scatter emissions 206, from the particles that are interrogated in the cuvette 204, are transmitted to the objective optics 208. The objective optics 208 create, in this example, five beams, rays, or images of fluorescence and side scatter, which are focused on the openings of the optical fibers 220, effectively projecting images of the sample locations onto the ends of the optical fibers. In this example embodiment, there are five laser beams 202, each of which intersects the sample at one of five different sample locations (not shown) in the cuvette. The particles that are present at each of these five separate sample locations may fluoresce differently, depending on the markers present in the sample and the characteristics of each laser beam 202. Thus, five distinct optical paths may be formed, each having light emitted predominantly from a different one of the sample locations. Mirror 214 directs the fluorescence and side scatter beams, rays, or images 218 from each sample location onto the corresponding ends of the optical fibers 220. The LED board 210 has an opening through which the five fluorescence and side scatter beams, rays, or images 218 are transmitted. The LED board 210 also has a set of LEDs 212 that generate various LED spectral outputs 216. In this case, since LEDs generally have an angular power distribution pattern, e.g., the light that is emitted from an LED is typically of highest intensity near the centerline of the LED and falls off as the angle between the light emission direction and the centerline increases, the close proximity of the LEDs to the edge of the opening allows the LEDs to satisfactorily illuminate the ends of the optical fibers, thereby allowing the calibration light to be coupled into the optical fibers at sufficient efficiency for delivery to the detectors, e.g., photomultiplier tubes (PMTs) 235, and detection thereby. While other types of light-emitting devices may be used in place of LEDs, e.g., lasers, such other types of light-emitting devices may require the use of additional optical components in order to direct the calibration light along the optical paths. It is to be understood that fewer or greater numbers of sample illumination sources, e.g., lasers, may be used in various embodiments.

The LED spectral outputs 216 that are transmitted from the LEDs 212 in an angular power distribution pattern may be reflected by the mirror 214 onto the ends of the optical fibers 220. The optical fibers may then transfer the LED spectral output 216, as well as the fluorescence and side scatter 218 (although typically not concurrently, as the calibration light may interfere with the sample light), to the five different spectral separators 222, 224, 226, 228 and 230. Each of the spectral separators 222-230 may, in this example embodiment, have up to eight different user replaceable optical filters, such as optical filter 233, each of which may be placed in front of one of the PMTs 235. The optical filters, such as optical filter 233, are user-replaceable so that the user can configure the spectral separators 222-230 for various different analyses. Since each spectral separator in this embodiment can have up to eight different optical filters 233 that are user-replaceable, there are a total of as many as 40 different optical filters in the flow cytometer 100 that may be able to be reconfigured. In some embodiments, as discussed later, there may also be dichroic mirrors used in a spectral separator that may also be user-replaceable, there may be additional optical filter elements (such as the dichroic mirrors) that may also be able to be replaced, leading to such a spectral separator having more than just 40 user-changeable optical filter elements in the depicted system of FIG. 4. It is to be understood that other embodiments may feature more or fewer spectral separators, as well as different numbers of user-replaceable optical filters and detectors or PMTs 235 than are shown in FIG. 4. This disclosure is not limited to flow cytometry systems using any particular number of spectral separators and/or detectors and/or optical filters.

If an incorrect optical filter is used, or if an optical filter is changed out and no record of its replacement is made, false positives and/or false negatives may occur when scanning particles. Additionally, repeatability of scans is also beneficial. For example, if one particular experiment is run day after day, it is desirable to have repeatability. To that end, as discussed later, the calibration light source may be operated at the same settings each day (or other regular interval of time) and the detector response may be checked to see if there has been any degradation in detector performance. The calibration light source, e.g., LEDs 212 on the LED board 210, may be used to check the responses of the PMTs 235, as well as to check for the use of the correct filters in the spectral separators 222-230. The manner in which the optical filters may be checked using the calibration light source is explained in more detail below with respect to FIGS. 8A-8C. Other uses include supporting instrument troubleshooting, having a spectral reference to standardize instrument-to-instrument performance, and having a spectral reference to translate detector output values into quantitative light detection values. These uses could be further enhanced by varying the intensity of the LED outputs. Referring again to the example embodiment FIG. 4, the spectral separator 222 includes a plurality of dichroic mirrors, such as dichroic mirror 237. As shown in the example system of FIG. 4, seven dichroic mirrors 237 are in each spectral separator 222-230. The dichroic mirror 237 reflects light having certain optical frequencies and transmits light having other optical frequencies, thus acting as both a beam-splitter and optical filtering device. In this manner, the seven different dichroic mirrors 237 in each spectral separator 222-230 divide the light transmitted from the optical fiber that delivers sample or calibration light to that spectral separator by spectral frequency and transmit the separated light to eight different optical filters, such as the optical filter 233. It is to be understood that in the depicted embodiment, the filtering that the sample or calibration light undergoes as it transits each optical path may include four separate filtering stages—three filtering operations that occur as a result of dichroic mirrors, and a final filtering operation that occurs as a result of the optical filter 233. It is to be understood that other types of beam-splitting devices may be used as well, e.g., beam splitters that do not have a dichroic effect—in such instances, the optical filters 233 may be the only optical filtering devices along the optical paths that act to filter the sample or calibration light reaching the detectors/PMTs. In some instances where dichroic mirrors are used, all of the dichroic mirrors may be "fixed," i.e., not user-replaceable. In other instances, all or at least some of the dichroic mirrors may be user-replaceable, with the remaining dichroic mirrors (if any) being fixed.

As also illustrated in FIG. 4, a plurality of photomultiplier tubes, such as PMT 234, are disposed to detect the light transmitted through the optical filters, such as optical filter 233. The optical filters 233 may be bandpass, longpass, or shortpass filters that only transmit light within a specific frequency range. In this manner, the fluorescence or side scatter from the cells is detected within a specific frequency range of the optical filter 233 by the PMT 235 (this is the case for each PMT 235 and corresponding optical filter—each may be configured differently to detect different wavelengths or frequencies of light). The existence and intensity of the light detected by the PMT 235 provides information regarding the characteristics of the particle that has been interrogated. In this manner, numerous different frequencies of the fluorescence and side scatter can be detected to identify these characteristics of the particle.

As noted earlier, a single sample illumination source, such as one of the laser beams 202, may create numerous fluorescent emissions. In the example given in FIG. 4, five different laser beams are used as sample illumination sources; these sample illumination sources produce five fluorescence and side scatter emissions 206 at the output of the cuvette 204; these five fluorescence and side scatter emissions 206 pass through the objective optics 208 leaving as five fluorescence and side scatter beams, rays, or images 218 that are focused on the ends of the optical fibers 220. Each of these beams, rays, or images, such as the fluorescence and side scatter beam, ray, or image 219, may contain light resulting from a number of different spectral responses of the fluorochromes used in the sample. For example, a 405 nanometer laser may create up to seven different fluorescent responses and one side scatter response. If the fluorescence and side scatter beam, ray, or image 219 from the 405 nanometer laser is focused on the end of the optical fiber 221, the beam 219, ray, or image is transmitted by the optical fiber 221 to the spectral separator 222. Each of the eight different spectral responses may be divided up by frequency using the dichroic mirrors, such as dichroic mirror 237, and each of the spectral responses may then be filtered by a separate optical filter disposed adjacent to the corresponding photomultiplier tube. Since there are eight photomultiplier tubes and eight optical filters, each of the spectral responses resulting from interrogation by the 405 nanometer laser may be detected in the spectral separator 222. Spectral separators 224, 226, 228 and 230 are also set up in a similar manner to detect up to eight spectral responses, e.g., spectral responses triggered by sample illumination sources having different wavelengths and/or originating from other fluorochromes. Of course, more or fewer detectors can be used in any one of the spectral separators 222-230, depending upon the expected spectral responses and the space in the flow cytometer that is allocated for the layout of the dichroic mirrors, optical filters, and photomultiplier tubes. As hinted at earlier, instead of dichroic mirrors, the sample or calibration light may also be separated using other means, such as refractive prisms, diffractive gratings, or holographic elements.

Figure 5:
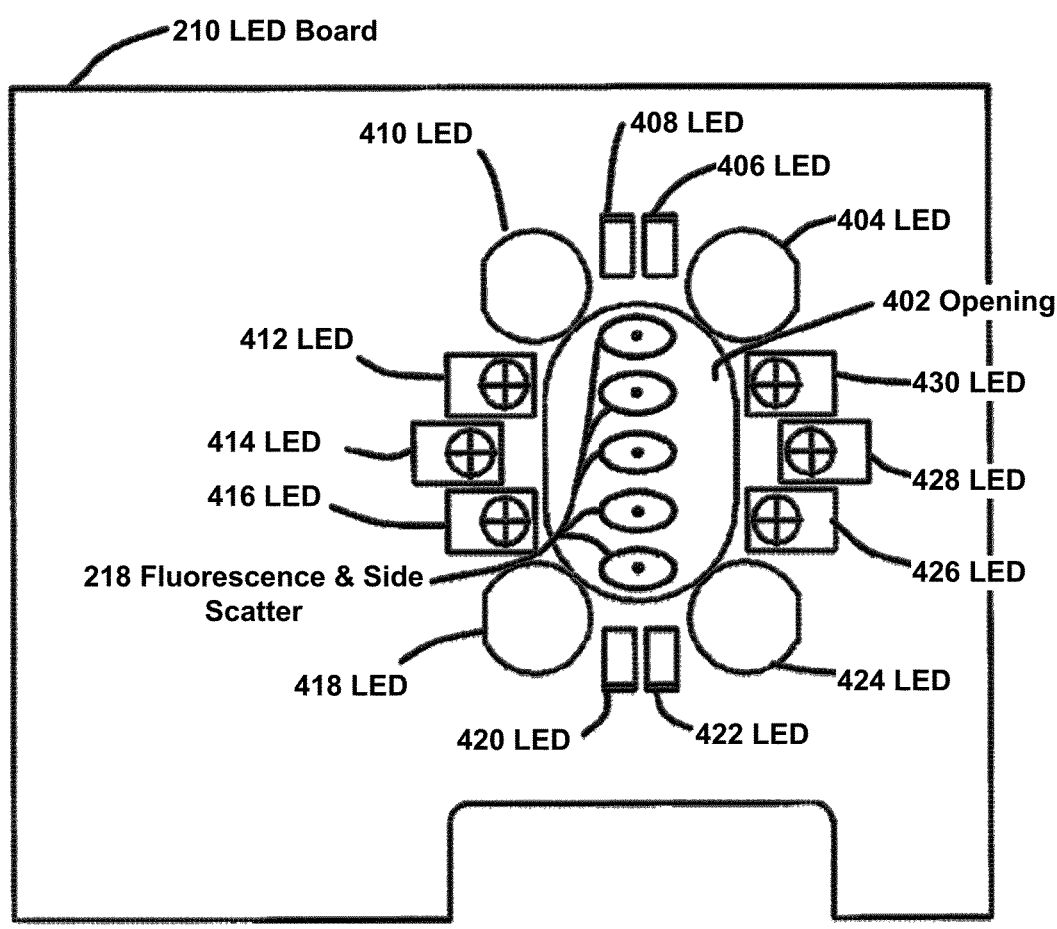
FIG. 5 is a plan view of an example embodiment of an LED board.

FIG. 5 is a schematic illustration of the layout of an LED board 400. As illustrated in FIG. 5, the LED board 210 has an opening 402 that allows beams, rays, or images of fluorescence and side-scatter, such as the five separate beams, rays, or images of fluorescence and side scatter 218, to be transmitted through the LED board 210. In this example, the five fluorescence and side scatter beams, rays, or images 218 are projected through the opening 402, as illustrated in FIG. 5. The spacing of the fluorescence and side scatter beams, rays, or images 218, in this particular example, results in a linear array of beams, rays, or images 218 that causes the opening 402 to be obround in shape, as illustrated in FIG. 5-depending on the arrangement of the beams, rays, or images 218 in a particular flow cytometer, the opening 402 may be shaped differently. As also illustrated in FIG. 5, there are a plurality of LEDs 404, 406, 408, 410, 412, 414, 416, 418, 420, 422, 424, 426, 428, 430 that are attached to the LED board 210 around the periphery of the opening 402. The LEDs 404-430, in this example, emit ten different spectral outputs corresponding to the spectral outputs illustrated in FIG. 8A. LEDs 404, 406, 408, 410, 412, 414, 416, 426, 428, and 430 all have different spectral outputs from one another. LEDs 404, 406, 408, 410 are repeated on the bottom portion of the LED board 210. The repeated LEDs are LEDs 424, 422, 420, 418, respectively. The reason why these LEDs are repeated on the top and bottom of the LED board in this example is that the acceptance or capture area of some of the ends of the optical fibers is not sufficiently large enough to capture light emitted from some of the LEDs 404, 406, 408, 410, 412, 414, 416, 426, 428, and 430. This is explained in more detail with respect to FIGS. 6 and 7.

As shown in FIG. 5, the opening 402 is centrally located with respect to the LEDs 404-430, which surround the peripheral portions of the opening 402. The LED board 210 may be a printed circuit board, which may be designed to be mounted and fixed along the optical paths at the output of the objective optics 208. As such, the LED board does not obstruct sample light and thus movement of the LED board is not required when switching between measurement of calibration light and sample light. The purpose of mounting the LED board 210 in the optical paths of the fluorescence and side scatter beams, rays, or images 218 is so that the LEDs 404-430 can project optical radiation onto the ends of the optical fibers 220, thereby directing the calibration light emitted from the LEDs 404-430 along at least a portion of the same optical paths.

As noted earlier, the LEDs 404-430 may typically emit light that has an angular power distribution. The emission angle, e.g., the total angle over which the light intensity of emitted light is 50% or higher of the peak light intensity value of the LED, for each of the LEDs 402-430 may vary, but a typical emission angle, for example, may be 120°. As such, the magnitude, e.g., intensity, of the light that is projected from the LEDs onto the ends of the optical fibers 220 may be substantially less than the total magnitude of light output from each of the LEDs. However, as explained in more detail below, the magnitude of light from each of the LEDs that is projected onto the ends of the optical fibers 220 may be in the same light magnitude range as that of the fluorescent and side scatter beams, rays, or images 218 that are projected onto the ends of the optical fibers 220, e.g., on the order of hundreds of microwatts to tens of picowatts. As such, the operating ranges of the photomultiplier tubes does not have to be altered to detect either the fluorescence and side scatter beams, rays, or images 218 or the calibration light/spectral signals from the LEDs 404-430.

Figure 6:
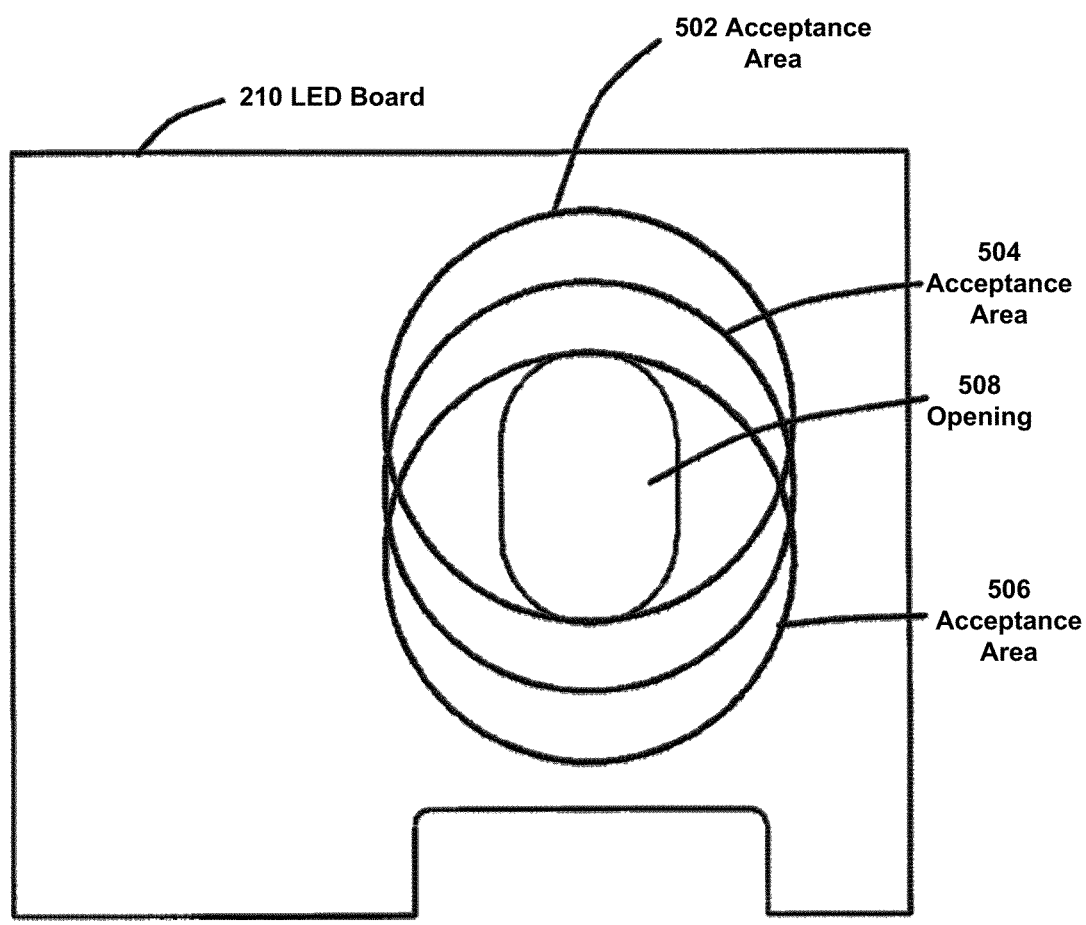
FIG. 6 is a schematic representation of an example LED board with acceptance areas of the optical fibers projected onto the LED board.

FIG. 6 is a schematic illustration of the LED board 210 with various capture areas, or acceptance areas, of the optical fibers projected onto the LED board 210. The capture or acceptance area of each optical fiber represents the area within which light from the LED board 210 may be emitted towards the end of the optical fiber and still be "captured" by the optical fiber, i.e., transmitted by the optical fiber. If the angle between an incoming light ray and the optical fiber centerline at the optical fiber end is too great, then the light ray will be rejected by the optical fiber and not be guided by the optical fiber. Thus, the acceptance or capture area of each optical fiber represents the area within which light may be emitted at an angle that is within the acceptance angle of the optical fiber end and also still intersect the optical fiber end. Another way of thinking of the acceptance area is as the projection area of the optical fiber end, i.e., if light were to be emitted out of the optical fiber through the optical fiber end, the acceptance area would be the area on the LED board that is illuminated by that light—this projected light would form a conical projection volume bounded by the acceptance angles of the optical fiber end.

As shown in FIG. 6, the opening 508 is present in LED board 210 to allow the fluorescence and side scatter beams, rays, or images 218 to be transmitted through the opening 508 in the LED board 210. Acceptance area 502 and acceptance area 506 represent the acceptance areas of the outer two optical fibers in the optical fiber bundle 220. For example, acceptance area 502 may correspond to the projection of the acceptance angles of optical fiber 221 onto the LED board. Similarly, acceptance area 506 may correspond to the acceptance angle of optical fiber 223 projected onto the LED board 210. Acceptance area 504 may correspond to the projection of the acceptance angle of the optical fiber 225, which is the center optical fiber. In that regard, placement of LEDs within the acceptance areas 502, 504, 506 will ensure transmission of the optical radiation from those LEDs into the corresponding optical fiber.

Figure 7:
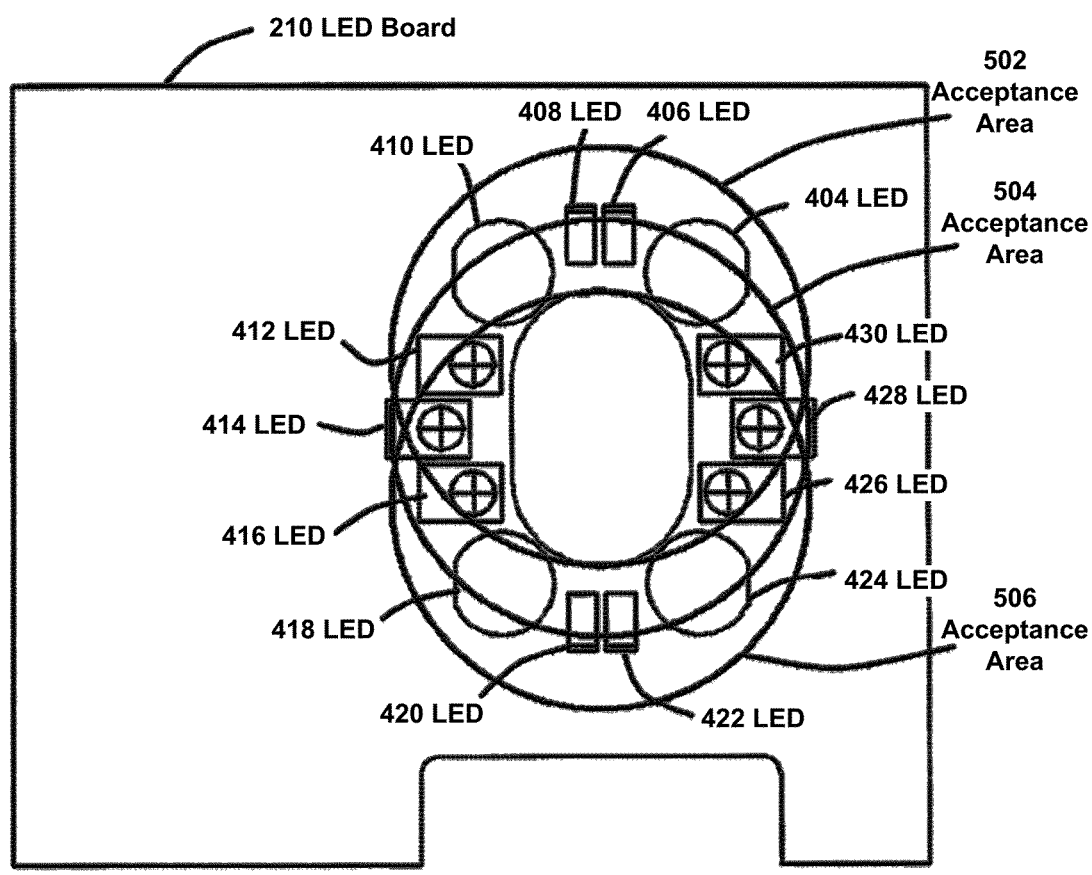
FIG. 7 is a schematic diagram illustrating the acceptance areas of the optical fibers that are projected onto the LED board relative to the locations of the LEDs in accordance with one example embodiment.

FIG. 7 is an illustration of the LEDs 404-430 placed on the LED board 210 with the three acceptance areas 502, 504, and 506 projected onto the LED board 210. Assuming that acceptance area 502 corresponds to optical fiber 221, calibration light emitted from LEDs 404-416 and 426-430 may be captured by optical fiber 221. Assuming that acceptance area 506 corresponds to optical fiber 223, calibration light from LEDs 412-430 may be captured by optical fiber 223. Similarly, calibration light emitted from LEDs 412, 414, 416 and 426, 428, 430 may be captured by all of the different optical fiber cables 220. To ensure that calibration light of the wavelengths emitted from LEDs 404, 406, 408, and 410 is also captured in all of the optical fibers, these LEDs are repeated at the bottom of the LED board 210 as LEDs 418-424, respectively. When any of the LEDs 404-410 are turned on, e.g., flashed (only a short duration of illumination is required, although longer illuminations may also be performed if desired), the corresponding LED of LEDs 418-424 is also turned on, respectively, so that all of the optical fibers receive the same wavelengths of calibration light simultaneously. The amount of power that is transmitted into the ends of the optical fibers 220 from the LEDs can be calculated by knowing the characteristics of each of the LEDs. For example, an LED that produces 250 mW of light energy with 75% of this energy within a 60° cone (120° total conic angle) that is centered on the center axis of the LED (perpendicular to the LED board, for example) can be used as a first example. At a distance of 125 mm between the LED and the end of the optical fiber, the cone has a 216.5 mm radius and covers an area of 147,262 mm$^2$. If the optical fiber has an end diameter of 1.5 mm, the area of the opening of the optical fiber is 1.77 mm$^2$. By dividing the total power of light energy emitted within the cone of interest by the area falling within the cone-of-interest at the same offset distance from the LED as the fiber end, and then multiplying that result by the area of the optical fiber end, the amount of light projected onto the optical fiberend can be calculated. In this example, 1.77 mm$^2$*(0.75*250 mW/147,262 mm$^2$)=approximately 0.0023 mW=approximately 2.3 µW. In this example and in the following examples, the illumination field is assumed to be uniform within the illumination cone, although in actual practice, the illumination may vary with distance from the illumination area center. More accurate determinations of the amount of light delivered to each optical fiber may be obtained, for example, by calculating the amount of light projected into an annular ring (at the same distance from the LED as the optical fiber) with a thickness equal to that of the optical fiber diameter and a radius defined by the distance from the optical fiber to the center of the illumination field and then using that value times the cross-sectional area of the optical fiber divided by the area of the annular ring. As another example, a 2.5 mW LED with 75% of its energy within a 15° cone (30° total cone angle) can be used. At a spacing of 125 mm between the LED and the end of the optical fiber, the illuminated region of the cone has a radius of 33.5 mm and an illuminated area of 3524 mm$^2$. Again, assuming that the optical fiber has an opening of 1.77 mm$^2$, the amount of light transmitted into the opening of optical fiber is 1.77 mm$^2$* (0.75*2.5 mW/3524 mm$^2$)=approximately 1 µW of power that is transmitted into the end of the optical fiber. As another example, a 5.5 mW LED has 75% of its energy within a 35° cone (70° total cone angle). At a distance of 125 mm between the LED and the end of the optical fiber, the area illuminated by the cone has an 87.5 mm radius and an area of 24,067 mm$^2$. The amount of light energy that is transmitted to the end of the optical fiber may be calculated as 1.77 mm$^2$*(0.75*5.5 mW/24,067 mm$^2$)=0.00030 mW=0.3 µW. The fluorescence and side scatter beams, rays, or images that are focused on the ends of the optical fibers 220 in such an example flow cytometer may have an incident power on the ends of the optical fibers 220 that is in the range of approximately one to three microwatts or less. Accordingly, the response of the photomultiplier tubes does not have to be altered, since the incident optical input power is in the same range for both the calibration light sources and the focused fluorescence and side scatter beams, rays, or images.

In some embodiments, the calibration light source may include a large number of ultra-narrow-band, e.g., on the order of 1-2 nm bandwidth, light sources, e.g., lasers. Each such light source may be used to test the optical filter paths at a different ultra-narrow-band wavelength, thereby allowing the characteristics of the filters along each optical filter path to be developed with an accuracy of a few nanometers or less. However, such embodiments may, if designed to cover a large working range of potential optical filters, be quite expensive. For example, covering a range of 550 nm, e.g., for optical filters from 350 nm to 900 nm, might require 250 to 550 different light sources and associated control hardware.

In alternative embodiments, such ultra-narrow-band light sources in the calibration light source may be replaced by light sources having larger emission bandwidths, e.g., LEDs having bandwidths on the order of tens of nanometers to between 100 and 200 nanometers. Such embodiments may be much more cost effective since a much smaller number, and less expensive, light sources may be used, e.g., 10 LEDs may be used to determine filtering characteristics within the 350 nm to 900 nm range of light. Such an embodiment is discussed in more detail in the following sections.

Figure 8A:
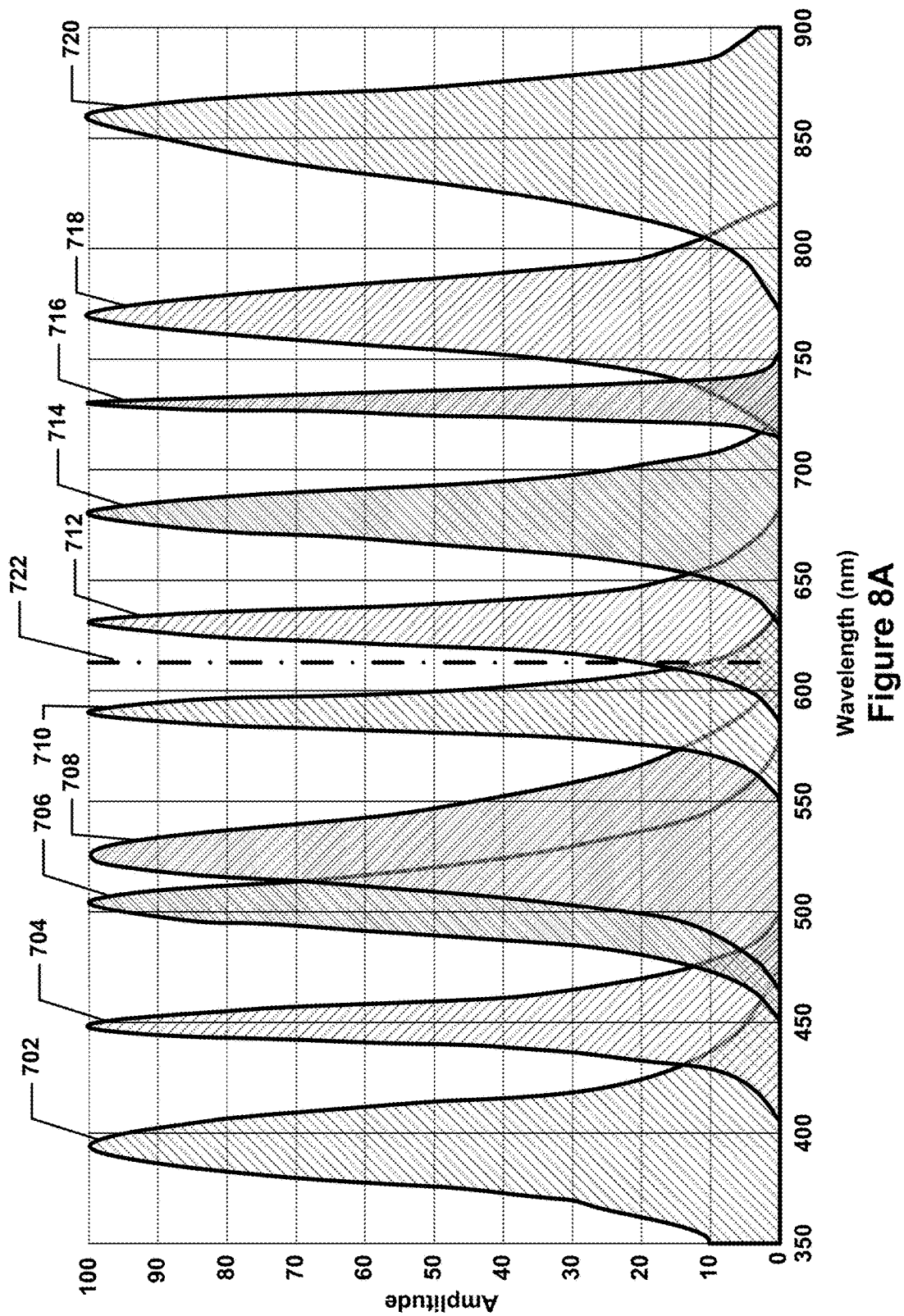
FIG. 8A is a graph of the LED spectral profiles.
Figure 8B:
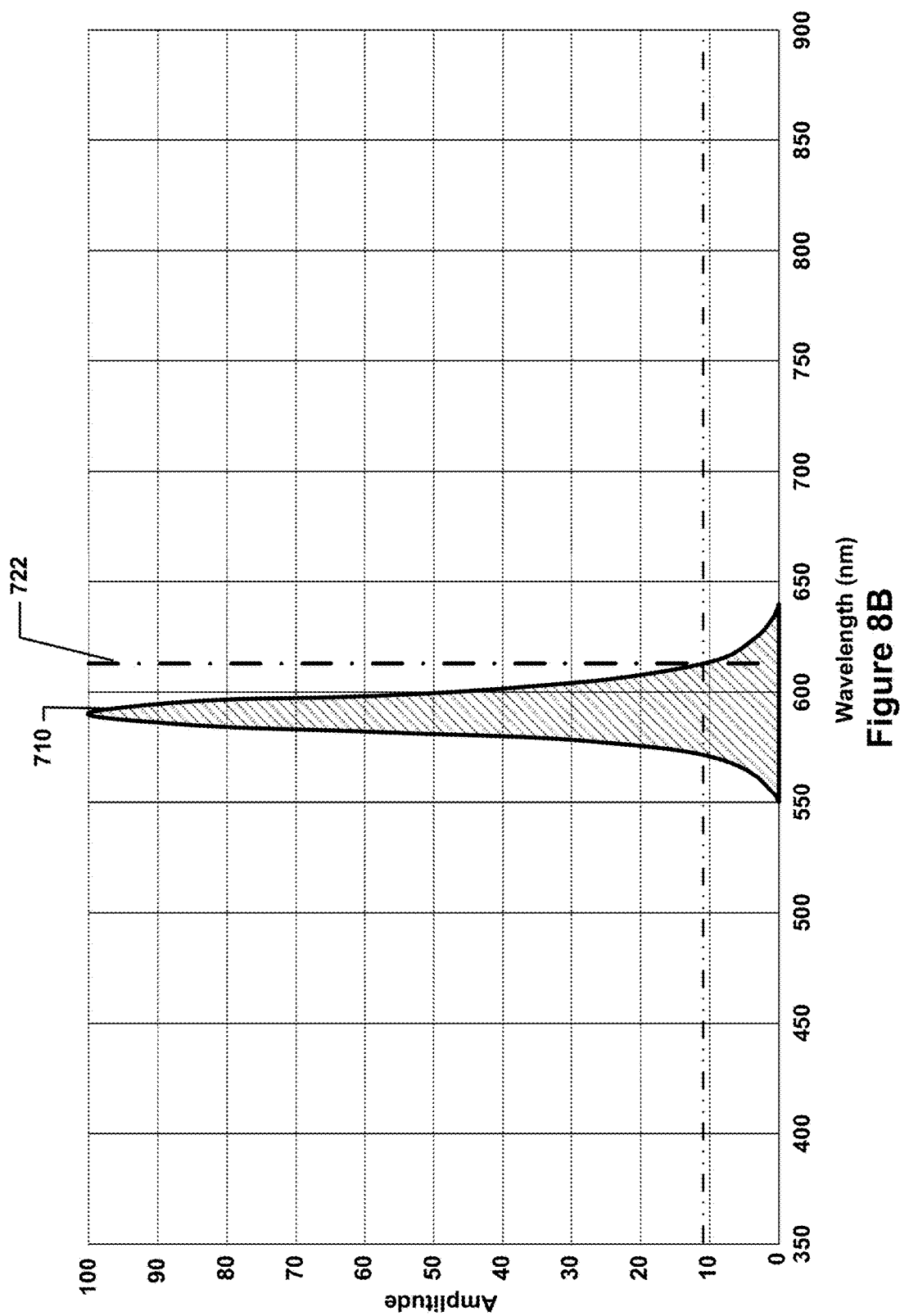
FIG. 8B is a graph of only one of the LED spectral profiles of FIG. 7A.
Figure 8C:
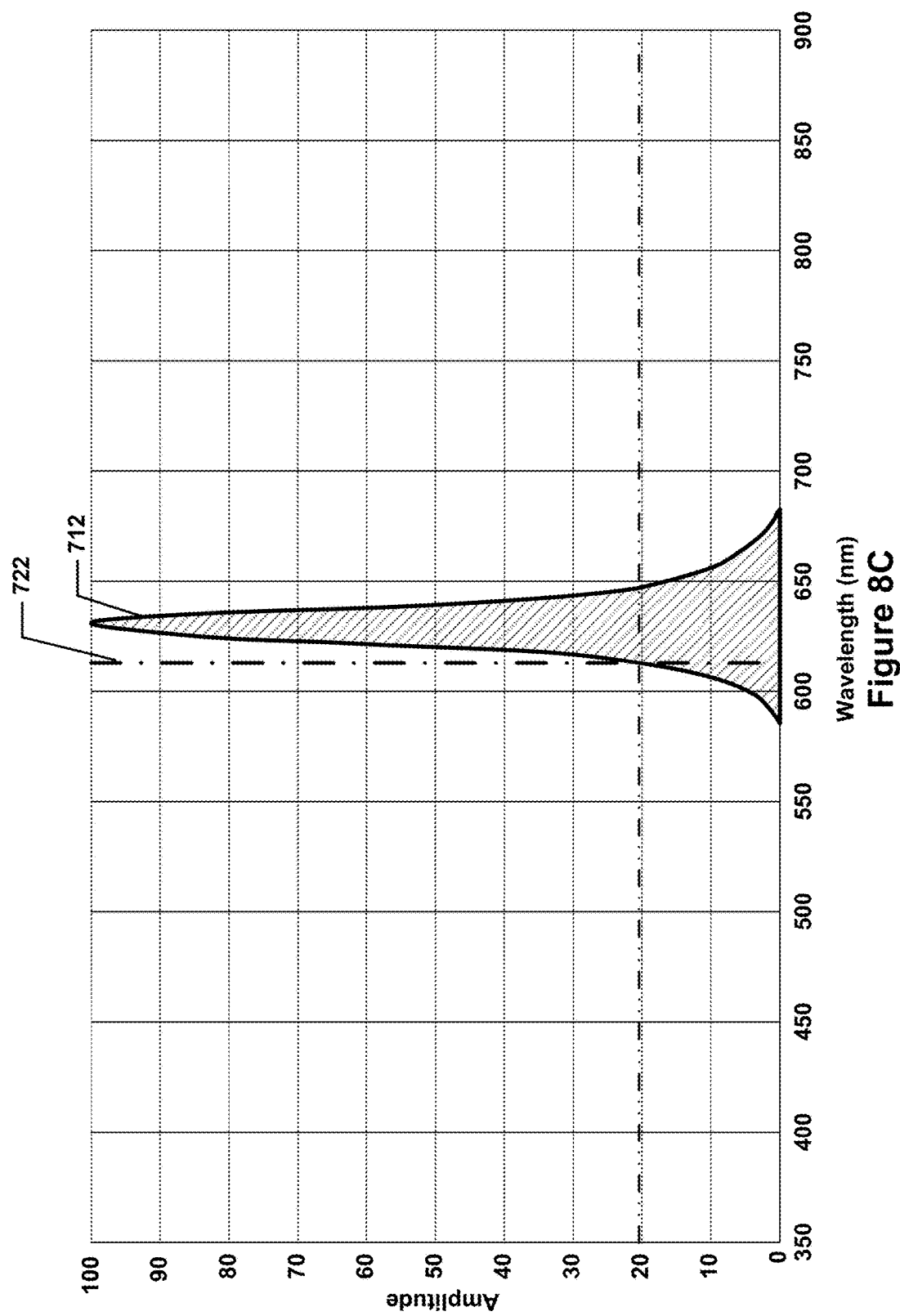
FIG. 8C is a graph of another one of the LED spectral profiles of FIG. 7A.

FIG. 8A is a graph of the ten different spectral outputs or profiles of the LEDs 404-430. As shown in FIG. 8A, the spectrum of the LED outputs goes from approximately 350 nanometers to 900 nanometers. The ten different spectral outputs or profiles include spectral profiles 702, 704, 706, 708, 710, 712, 714, 716, 718 and 720. The spectral profiles 702-720 have different spectral ranges that vary from about 150 nm to about 30 nm. At peak output powers, the spectral profiles range from about 40 nm in bandwidth to about 10 nm in bandwidth. These are examples of what may constitute a narrowband optical frequency, although various different spectral profiles can be used. The ten different spectral signals 702-720 allow the flow cytometer to determine the optical or filtering characteristics of the optical filters that are in the various locations shown in FIG. 4 (as used herein, "characteristics," "optical filtering characteristics," "optical characteristics," and "filtering characteristics" are all used to refer to the optical properties of an optical filter element or elements that govern the filtering capabilities of that optical filter element or elements—it may refer to a particular center wavelength of the filter element or a broader set of wavelengths that the filter element may transmit). For example, if an optical bandpass filter is used having a center wavelength 722 of 620 nm, the detector that receives light that passes through such an optical filter should produce an output signal when the LED(s) having the spectral profile 710 are illuminated (and the other LEDs are dark) and a slightly larger output signal when the LED(s) having the spectral profile 712 are illuminated (and the other LEDs are dark). This is because the LED(s) having the spectral profile 712 emit slightly more light at the 620 nm wavelength than the LED(s) having the spectral profile 710. The existence of some response from spectral signal 710 assists in identifying the frequency or wavelength of the optical filter in this example. For example, if the detector detects light when the LED(s) having the spectral profile 710 are illuminated, then such information indicates that whatever optical filter is installed is transmissive to light having a wavelength falling within the spectral profile 710. In some instances, the calibration light source may be configured to emit known intensities of calibration light. In such instances, if the intensity of emitted calibration light is known, then the amount of calibration light that is detected by the detector in response to such calibration light emission may be used to further identify the optical characteristics of the optical filter. For example, if the detector registers that the amplitude or intensity of the detected calibration light emitted from the LED(s) having the spectral profile 710 is approximately 11 (based on the unitless scale used in FIG. 8A—see FIG. 8B), there are only two wavelengths of light that are emitted by such LEDs that produce such an amplitude—approximately 570 nm and approximately 620 nm. By illuminating other LEDs corresponding to other spectral profiles, however, further information may be obtained that permits for a more definite characterization of the optical filter in question. For example, if the LEDs that produce the spectral profiles 702, 704, 706, 714, 716, 718, and 720 are illuminated, either separately or in combination, none of the light emitted from those LEDs would pass through the optical filter with the center wavelength of 620 nm (assuming that the overall bandwidth of this filter is relatively narrow, e.g., no more than ±10 nm). Furthermore, if the LED(s) that produce the spectral profile 712 are illuminated (with the other LEDs dark), the detector may, for example, indicate a measured light amplitude of approximately 21 (see FIG. 8C). By comparing the ratio of detected light amplitude for two neighboring/overlapping spectral profiles, a determination may be made as to which center wavelength corresponds with the calculated ratio. For example, there is only one optical filter center wavelength at which the light from the LED(s) that produce the spectral profile 710 that reaches the detector will have approximately half the amplitude of the light from the LED(s) that produce the spectral profile 712 that reaches the detector—the center wavelength 722 (620 nm). These ratios may be compared against a lookup table of expected ratios for each wavelength (each ratio would thus be associated with a particular wavelength and with the spectral profiles emitted by the calibration illumination source for each emission of calibration light resulting in a measured calibration light amplitude contributing to that ratio).

Alternatively, each optical filter element (or each optical filtering characteristic) may have a "fingerprint" of expected measured magnitudes associated with calibration light emitted with each of the spectral profiles. By comparing the measured amplitudes for calibration light of each spectral profile against a database of such fingerprints, a determination may be made as to whether the measured amplitudes correspond to a particular optical filter element fingerprint, thereby allowing the optical filter element to be characterized and identified. It is to be understood that the matching of ratios or amplitudes to data from lookup tables or other data sources may be facilitated through the use of tolerances or other mechanisms that account for the potential for measurement error and other factors that may affect the measured value. The same fingerprinting technique may also be applied to a set of multiple optical filter elements arranged in optical series, with the fingerprint being representative of the cumulative filtering characteristics of the set of multiple optical filter elements. In embodiments where light sources with ultra-narrow-band spectral profiles are used, it may be possible to have a one-to-one match between a particular optical filtering characteristic and a single spectral profile, in which case that optical filtering characteristic may be determined if there is any output signal from a detector in response to calibration light of that spectral profile. In some further such embodiments, the filtering characteristics of optical filter elements along a particular optical path may have a broader bandwidth than that of the spectral profiles used for the calibration light source in the vicinity of the optical filter elements' center frequency. In such cases, it may be the case that several of the spectral profiles that the calibration light source may be able to emit may result in the detector for that optical path detecting the calibration light emitted. Thus, for example, the detector may detect the same magnitude of detected calibration light responsive to calibration light independently being emitted at several different spectral profiles. In such cases, it may be difficult to determine which of these spectral profiles is most representative of the optical filtering characteristics of that optical path, as there may be multiple candidates, all of which may produce similar output signals from the detector. In some such embodiments, all of the spectral profiles at which the calibration light results in a certain minimum threshold level of output signal may be identified and used to characterize the optical filtering characteristics of that optical path. For example, if calibration light of seven adjacent spectral profiles all independently produce similar output signals from the detector, then the wavelength associated with the center spectral profile, e.g., the fourth spectral profile of the seven in this example, may be identified as the center wavelength of the optical filter element(s) along that optical path. If there is an even number of such spectral profiles, then the center wavelength may be the average of the two center-most spectral profiles.

For example, FIG. 8D is a table of spectral fingerprints using the LED spectral profiles of FIG. 7A. In this example, the table includes spectral fingerprints at 10 nm intervals across the spectrum of 400 nm to 850 nm. Each row represents a spectral fingerprint that corresponds with a different wavelength. Each column lists the measured light intensities at each of those different wavelengths for a different spectral profile of calibration light. For example, if the calibration light source is caused to separately emit each of the spectral profiles 702-720, and the measured light magnitude or intensity at a detector is 14 for spectral profile 706, 64 for spectral profile 708, and 0 for all of the other spectral profiles, then this may indicate that the filtering characteristics for the optical path leading to that detector correspond with filtering characteristics for a 540 nm filter, which has a fingerprint in which spectral profile 706 results in a magnitude of 15, spectral profile 708 results in a magnitude of 68, and the other spectral profiles result in a magnitude of 0. As can be seen, there may be some degree of mismatch between the ideal fingerprint for a particular wavelength and what is measured (at spectral profile 706, a measured intensity of 14 as compared with a fingerprint intensity of 15, for example). Such minor variations may be accommodated by any of a variety of techniques known in the art, e.g., the use of tolerance bands, interpolation, pattern matching techniques, etc. As discussed earlier, the ratio concept discussed above may also be implemented as part of a lookup table; this may be similar, in effect, to the fingerprinting technique, but may allow for variable detector sensitivity. For example, two detectors may have different sensitivities to light, e.g., one may not be performing at peak performance and may therefore underreport the amount of light that reaches it. In order to accommodate such detector sensitivity, the absolute magnitude of the light that is detected may be converted into a relative magnitude based on the magnitude of light in an adjoining spectral profile, much as is discussed above with respect to the use of ratios. This, in effect, may normalize the detector response so that detector sensitivity does not cause mismatches between the detected light intensity and the expected light intensity.

For example, if a detector is underreporting the magnitude of light that reaches the detector by 50% in the preceding example, the measured light magnitude would be 7 for spectral profile 706, 32 for spectral profile 708, and, of course, still 0 for the remaining spectral profiles. These measured light magnitudes would not, however, correlate well with any of the expected light magnitudes as listed in the fingerprint table of FIG. 8D. The closest would be the fingerprint for 550 nm, which has an expected light magnitude of 8 at spectral profile 706 and 44 at spectral profile 708. For spectral profile 708 in particular, the value of 32 is 30% lower than the expected value of 44.

Such issues may, in some implementations, be resolved by using the ratios of the measured light magnitudes for adjoining spectral profiles. For example, the ratio of the measured light magnitude for spectral profile 706 to that of spectral profile 708 is 7:32, which equals 0.22. If that ratio is compared to corresponding ratios based on the expected light magnitudes for those two spectral profiles, it can be seen that the proper wavelength of 540 nm can be easily identified despite the decreased light magnitude that is detected. For example, the ratio of the expected light magnitude at spectral profile 706 to that of spectral profile 708 for the 540 nm wavelength is 15:68, which also equals 0.22. In comparison, the ratio of the expected light magnitude at spectral profile 706 to that of spectral profile 708 for the 550 nm wavelength is 8:44, which equals 0.18, and the ratio of the expected light magnitude at spectral profile 706 to that of spectral profile 708 for the 530 nm wavelength is 30:97, which is 0.31. Such normalization may thus allow for accurate determination of the optical characteristics of the optical filter elements along the optical path even when the detector is operating at an unknown level of efficiency. It is to be understood that a variety of other techniques for matching measured light detected in response to light from each of the spectral profiles being emitted to a spectral fingerprint may be used as well, and are considered to be within the scope of this disclosure. The examples discussed herein are representative examples and not to be viewed as limiting.

It is also to be understood that while the examples discussed herein have focused on spectral profiles that generally only overlap with one or both immediately neighboring spectral profiles, the same techniques may be practiced using a larger number of overlapping spectral profiles, e.g., spectral profiles that overlap with more than one other spectral profile on either or both sides. In such cases, there are simply further data points to populate the spectral fingerprints with and against which to compare measured light magnitudes.

Additionally, in the examples discussed herein, the optical filtering characteristics have generally been assumed to be those of narrowband optical filters, e.g., tightly constrained to a single center wavelength. The same techniques may, however, generally be used to identify other types of optical filtering characteristics, such as those associated with wider-band filters.

It is to be understood that the calibration light source, at a minimum, should include light sources, e.g., LEDs or lasers, that may be controlled to independently emit calibration light of different spectral profiles, i.e., the calibration light that is emitted by the calibration light source may be switched between a number of different spectral profiles. In embodiments featuring the ability to emit a large number of spectral profiles, e.g., such as the ultra-narrow-band embodiment discussed earlier, the spectral profiles may be non-overlapping or only overlap to a minimal amount, e.g., across less than 10% of their base width.

In embodiments featuring wider spectral profiles, e.g., such as those depicted in FIG. 8A, each spectral profile may be selected to overlap with the neighboring spectral profile or profiles such that, for example, there is only one wavelength that is uniquely identified by the detector outputs produced in response to all of the spectral profiles being provided in isolation. For example, each of the spectral profiles in FIG. 8A has a somewhat Gaussian shape, and a given measured light amplitude of calibration light having one of these spectral profiles may, in locations other than the maximum amplitude, correspond with two potential wavelengths—one on the "upslope" of the distribution and the other on the "downslope" of the distribution. Because the spectral profiles overlap, the measured amplitude of calibration light for one or both neighboring spectral profiles may be used to determine whether the "upslope" or "downslope" wavelength is the correct wavelength. It is to be understood that, in some cases, there may be portions of a given spectral profile that do not overlap with a neighboring spectral profile (see, for example, spectral profiles 714 and 718, which have portions that do not overlap with the neighboring spectral profiles). Such spectral profiles may nonetheless allow for accurate characterization of an optical filter's characteristics if the non-overlapping portion does not have multiple data points corresponding to the same amplitude. For example, in FIG. 8A, the spectral profile 714 overlaps with the spectral profile 712 throughout the entire "upslope" portion (the portion to the left of the maximum amplitude) of the spectral profile 714. If a measured calibration light amplitude of 20 is detected in response to calibration light having the spectral profile 714 being emitted, then there are two potential wavelengths for the optical filter being characterized: ~610 nm and ~700 nm. If the calibration light source is then caused to emit calibration light having the spectral profiles 712 and 716, and neither such calibration light emission results in any measurable amplitude of light, then the 610 nm wavelength may be eliminated as a candidate, as the spectral profile 712 would have resulted in measurable light amplitude if the optical filter was transmissive to 610 nm light.

To facilitate discussion, the above analysis and example utilize a calibration light source in which every LED emits the same maximum amplitude of light, regardless of the wavelength of that maximum amplitude of light. It is to be understood that the spectral responses need not be of uniform maximum amplitude—different light sources of the calibration light source may emit different spectral profiles with different maximum amplitudes. If the spectral profiles (or spectral profile information) used in the determination of the optical filter characteristics are representative of the actual emitted calibration light, the determinations regarding optical filter characteristics based on such spectral profile data may nonetheless be accurate. It is also to be understood that corrections may need to be made if there are multiple LEDs used to generate a particular spectral profile—for example, if two LEDs are used to generate calibration light of a particular spectral profile, but only a proper subset of optical fiber ends receive light from both LEDs (with the remaining optical fiber ends only receiving calibration light from one LED), then the amplitude of detected light may be artificially halved (or doubled) at some detectors compared with other detectors. In such cases, the LEDs that are associated with that particular spectral profile may be illuminated separately (so that the amplitude at any detector receiving the calibration light is not "doubled" or "halved" compared to the light received at any other detector). Alternatively, the detected amplitude may be either halved or doubled, as necessary, in order to conform the signal to the spectral profile that is used as a reference. For example, if the spectral profiles are each specified for a single LED, and a particular detector receives light from two such LEDs, the output signal indicating magnitude may be halved in order to normalize the signal to the scale of the spectral profile. The output signals from detectors that do not receive light from two LEDs may be left alone. There are, it will be recognized, multiple other ways of accounting for such potential errors, all of which are considered to be within the scope of this disclosure.

In some instances, the above technique may not be able to determine the optical characteristics of a particular filter, but may instead be used to determine the optical characteristics of multiple optical filters as a whole—thereby allowing a determination of whether the optical filters as a whole are properly configured. For example, if two filters are arranged in series, each having a different center wavelength, the calibration light source may only be able to determine the combined optical characteristics of the two filters—the technique cannot be used to determine which of the two optical filters is which. If there is only one optical filter along a particular optical path, then, of course, the above technique may be used to positively characterize that particular filter.

The spectral profiles of the calibration light source may be determined based on published data, e.g., manufacturer-supplied spectral profile data, or empirically. For example, in some implementations, the flow cytometer may be placed into a baseline mode where a detector may be used to detect calibration light emitted at each of the spectral profiles using a known optical filter element or set of optical filter elements along that detector's optical path. The detected light magnitude readings associated with each spectral profile may then be recorded and used as the "fingerprint" for the optical characteristics of that known optical filter element or set of optical filter elements. There are typically only a set number of optical filter elements that are used with a flow cytometer, so the population of possible filtering characteristics that may potentially need to be detected may be limited; these possible filtering characteristics may be thought of as the optical characteristics of interest for a given flow cytometer system. Once all of the optical characteristics that are of interest have been fingerprinted, then further fingerprinting may, in some embodiments, be skipped, as such further optical characteristics may be very unlikely to ever be encountered during normal use (the errors that are typically encountered in configuring flow cytometers are errors in which the existing population of optical filter elements for the flow cytometer is somehow incorrectly configured within the flow cytometer, rather than situations where a rogue filter element from some other piece of equipment somehow makes its way into a flow cytometer optical path configuration). It may, from a practical standpoint, be sufficient to simply be able to identify when a filter element configuration has optical characteristics corresponding with one of the expected optical characteristics—if the measured light magnitudes are such that no match to a fingerprint of the expected optical characteristics is able to be made, then this may indicate that the filtering configuration, whatever it may be, is incorrect. In such cases, an alert may be provided by the calibration system to the user simply to indicate that there is an optical filtering configuration error, without any further specification of what the error is (aside from indicating which optical path has the error, assuming there are multiple optical paths being tested). In some other implementations, the system may identify the nature of the error as well, e.g., a notification may be provided to the user indicating that the optical path in question has optical filtering characteristics corresponding with a particular wavelength or wavelengths when it should have optical filtering characteristics corresponding with another particular wavelength or wavelengths. Of course, in some embodiments, fingerprints for optical filtering characteristics that are not expected to be encountered in normal use of the flow cytometer may also be included in the fingerprint database; in such embodiments, the notification to the user in case of a mis-configuration of an optical path may also include information regarding the optical characteristics of that optical path that correspond with the matching fingerprint.

Figure 9:
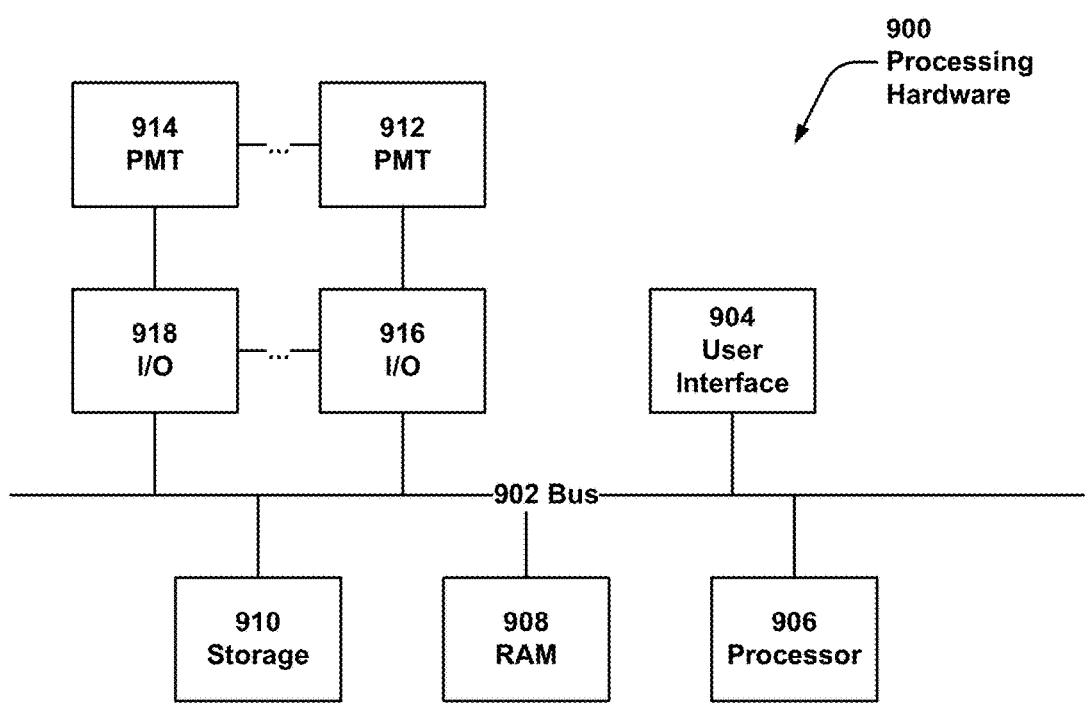
FIG. 9 is a schematic block diagram of processing hardware for one example embodiment.
Figure 10:
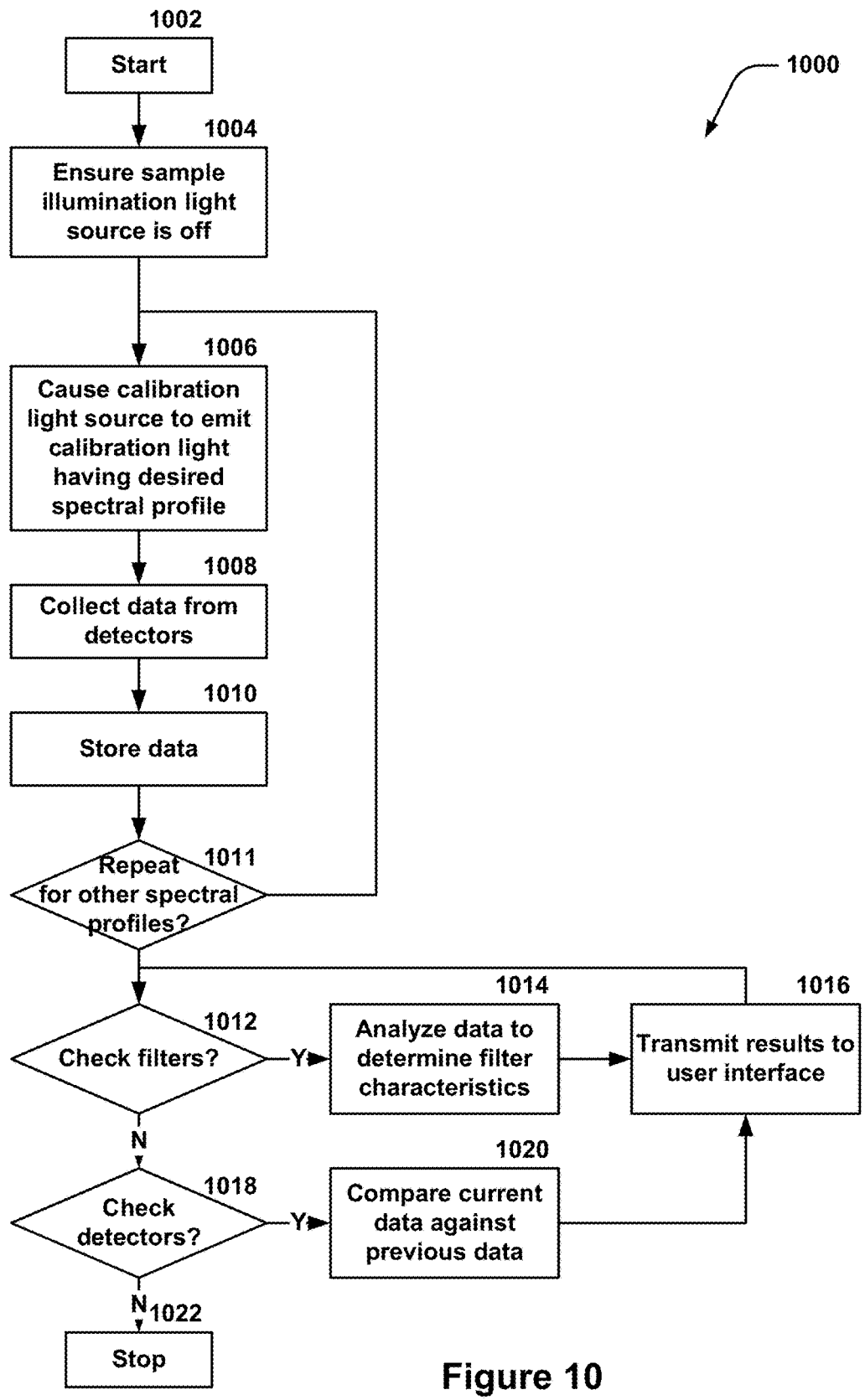
FIG. 10 is a flow diagram of the operation of the processor for one example embodiment.

FIG. 9 is a schematic block diagram of an embodiment of processing hardware 900 that can be utilized with the other embodiments disclosed herein. As illustrated in FIG. 9, a bus 902 is utilized as a backbone for the processing hardware 900. User interface 904 allows a user to operate and control the various functions of the processing hardware 900. Data from the photomultiplier tubes, which are schematically illustrated as photomultiplier tubes 912, 914, is transmitted to input/output devices, such as I/O 916 and I/O 918. This data is then transmitted along the bus 902 and stored in RAM 908 and/or storage 910. The processor 906 performs various processing functions, as illustrated in FIG. 10, such as comparing previous data with current data, current data with calculated data, and current data with empirical data. Other functions may also be performed by the processor 906. The results of these data comparisons may be provided to the user interface 904. The user interface 904 may also be used to control the sensitivity of the photomultiplier tubes that are schematically shown as PMT 912 and PMT 914 (there may be additional PMTs and I/O devices as well, but these are not shown).

FIG. 10 is a schematic flow diagram 1000 illustrating at least some of the functions of the processor 906. As illustrated in FIG. 10, the processor may start operation at step 1002. At step 1004, the processor may optionally check to ensure that the lasers or other sample illumination sources in the flow cytometer are off. At step 1006, the calibration light source may be illuminated. The calibration light source may be illuminated to produce light for one spectral profile, a subset of spectral profiles, or all spectral profiles that the calibration light source is capable of producing, depending on the testing desired or supported. For example, if optical filter testing is desired, then the calibration light source may be sequentially activated, e.g., LEDs producing different spectral profiles may be separately illuminated, in order to emit calibration light of each spectral profile that is supported by the calibration light source. However, if the calibration light source is instead being used to test the detectors against previous detector performance, then the calibration light source may be caused to produce calibration light for all of the spectral profiles simultaneously. At step 1008, the processor collects the data from the photomultiplier tubes as a result of the illumination by the calibration light source. At step 1010, the data from the detectors, e.g., PMTs, is stored. The data can be stored in the RAM 908 or in the storage 910. At step 1011, a determination may be made as to whether further illumination of the calibration light source is needed, e.g., to allow for additional calibration light of other spectral profiles to be generated. At step 1012, the processor may determine if the optical filter elements are to be checked, e.g., by checking for a user-specified setting or consulting a schedule or other rule governing the timing of optical filter element checks. If the optical filter elements are to be checked, the current data may be compared with stored data that is used for checking filters, e.g., the magnitude data from the detectors for each emission of calibration light at a particular spectral profile may be compared against stored data, as discussed earlier, to determine the optical characteristics of the optical filter(s) through which the detected light passed in route to the detector. At step 1016, the results of the comparison may be transmitted to the user interface. The results may vary, depending on the particular configuration of the system. For example, in some embodiments, the optical characteristics that are determined for an optical filter element or elements may be transmitted to the user interface and displayed to the user. In some other or additional embodiments, the optical characteristics may be compared against pre-defined expected optical characteristics that are associated with a particular setting of the flow cytometer, and discrepancies between the expected optical characteristics and the determined optical characteristics may be highlighted or otherwise indicated, thereby notifying the user that there is an anomaly. For example, a flow cytometer may have settings that allow the user to specify the type of fluorochrome(s) being used for a marker, and each such fluorochrome may be associated with a different set of optical filter characteristics that have been predetermined to be appropriate for accurate and reliable detection of fluorescence from such fluorochromes, When the user specifies a particular fluorochrome, the optical characteristics of the optical filter elements may be evaluated against the optical filter characteristics for that fluorochrome.

The process may then return to determine if the filters need to be checked (or may proceed directly to step 1018). Since the optical filter elements have been checked, the process may then optionally proceed to step 1018 to check to see if the detector operation should be checked. If it is determined in step 1018 that the detectors should be checked, e.g., a user setting or other rule specifies that such a check should occur, the process may proceed to step 1020, where the current data may be compared against previous test data to determine if there has been a change in performance of the flow cytometer. In this manner, if the current test data is the same, or nearly the same, as previous test data, the system can verify that the detectors are operating properly. For example, if all of the detectors exhibit similar responses to the same spectral profile(s) of calibration light, this may indicate that the detectors are performing consistently with respect to the earlier performance. If, however, one or more detectors exhibits a lower or higher response than the earlier test data indicates for the same spectral profile of calibration light, then this may indicate that the detectors in question are experiencing a fault of some sort, i.e., that there has been a change in optical performance in the system compared to the previous optical performance state of the system. These results may then be conveyed to the user via the user interface in step 1016 and the process may then return to step 1012. If it is determined that the filters do not need to be checked in step 1012 and that the detectors do not need to be checked in step 1018 the process may then proceed to step 1022, where the process is stopped. It is to be understood that the order of the above steps may be altered in some embodiments, and that some steps may be omitted in some other or additional embodiments. For example, some embodiments may not include functionality to test the detector performance, and such steps may therefore be omitted in some cases.

Additional processing may also be performed to check a variety of other operating parameters. For example, if a detector performance test indicates that all detectors that are provided light from a single optical fiber or pinhole have a decreased signal strength compared to an expected value or compared to measured signal strengths by other detectors in the system, such information may indicate an issue with the delivery of light to that spectral separator rather than an issue with the detectors themselves. For example, there may be a defect or fault in the optical fiber for those detectors. In another example, the calibration light source may be operated to obtain measured light values, followed (or preceded) by the flow of calibration particles having a known intensity of light emission in response to excitation by the sample light source. If the detectors register the light from the calibration light source without issue but register a decreased intensity of emitted light when the calibration particles are separately stimulated by the sample light source, such information may indicate that there is an issue with the sample light source, e.g., an excitation laser may be operating at decreased output, thereby causing decreased fluorescence in the calibration particles (as noted earlier, the calibration light source may be designed such that the calibration light that is transmitted to the detectors has a similar order of magnitude to the sample light that is expected to be measured by the detectors during normal use—thus, the calibration light may serve as a form of illumination standard or reference point against which other illumination may be compared, such as the calibration particle emissions).

In some embodiments, the actual spectral profile of each light source used in the calibration light source may be separately measured using a calibrated instrument, for example, a spectrometer. Such measurements may capture variations in spectral profile shape, as well as intensity for each light source, from a "nominal" spectral profile that may be expected for such light sources, e.g., such as a manufacturer's advertised spectral profile for an LED. These measured spectral profiles may then be stored in a memory that is associated with that particular calibration light source, e.g., a non-volatile memory that is on the printed circuit board of the calibration light source and thus travels with the calibration light source. The measured spectral profiles may then be used as the spectral profiles for the light sources in that calibration light source going forward, e.g., as the spectral profiles shown in FIG. 8A. Such a custom-calibrated calibration light source may be used to enhance the accuracy of optical characteristic determination in general and for any of the embodiments discussed herein.

In some embodiments, a single calibration light source may be used with multiple flow cytometers to help standardize or calibrate their performance. For example, the detectors used by flow cytometers may have varying sensitivity to the same intensity of detected light, i.e., may produce different output readings for the same input. In order to quantify such detector-to-detector variability, the same calibration light source may be moved from one flow cytometer to another and operated in both flow cytometers using the same settings. The resulting detector readings from both flow cytometers may then be compared, and the differences in detector sensitivity between the two flow cytometers may be quantified to allow the outputs from the detectors to be calibrated or standardized with respect to one another. Of course, more than two flow cytometers may be calibrated in this fashion as well. The same technique may also be used within a single flow cytometer to calibrate different detectors within that flow cytometer with one another. It is to be understood that during such inter-detector calibration operations, the optical paths leading to each of the detectors being calibrated should, ideally, be identical in terms of filtering characteristics, e.g., with no filters in place or with the same filters in place, so that differences in detector output due to differing filtering characteristics are not confused with differences in detector output due to detector sensitivity differences.

The calibration light source may thus be used as a common reference point.—by measuring the output signals that are produced by detectors in multiple flow cytometers in response to calibration light emissions produced by the same calibration light source using the same settings.

Figure 11:
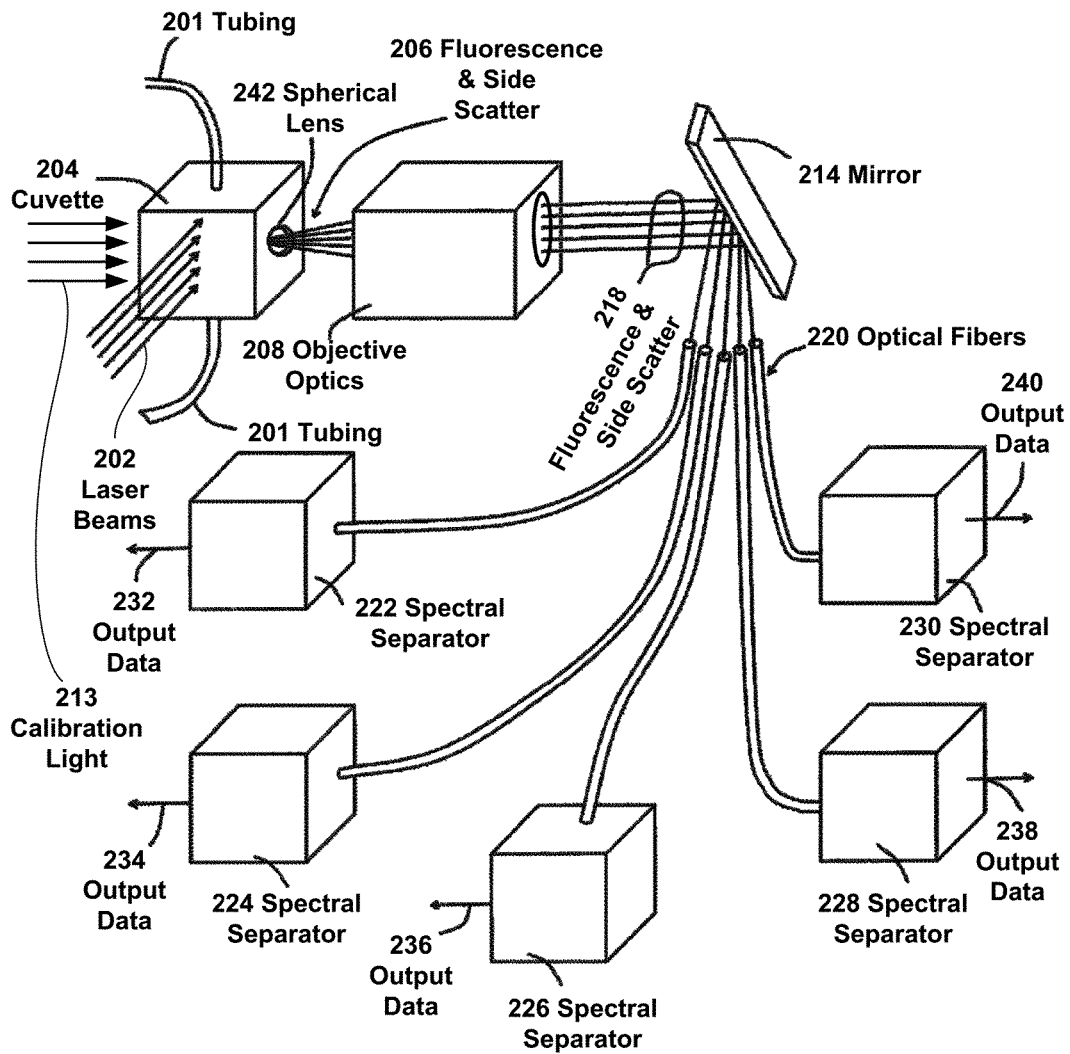
FIG. 11 is a schematic of a further embodiment of a flow cytometer.

One further embodiment that may be used to implement the systems and techniques discussed herein is illustrated in FIG. 11. FIG. 11 depicts a schematic of a flow cytometer that is similar to that illustrated in FIG. 2. However, instead of including an LED board as the calibration light source as shown in FIG. 2, the calibration light source is positioned so as to emit calibration light through the cuvette—thus, the calibration light and the sample light will follow the same optical paths, allowing for the entirety of the optical paths to be checked for potential defects. For example, if there is a defect in the objective optics 208 that may impact detector efficiency, the embodiment shown in FIG. 2 would not detect such a defect since the calibration light is introduced to the optical paths "downstream" of the objective optics. In contrast, the embodiment of FIG. 11 would be able to detect such a defect since the calibration light also travels through the objective optics 208.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A system comprising:
   a flow cytometer including:
   at least one sample illumination source, wherein each sample illumination source is configured to deliver light to a corresponding sample location, thereby causing sample light to be emitted by or scattered off of particles in the corresponding sample location;
   focusing optics that are configured to direct the sample light from each sample location along one or more optical paths, wherein each optical path passes through a corresponding one or more optical filter elements and terminates at a corresponding detector that is configured to produce output data indicative of the measured intensity of light reaching that detector;
   a calibration light source that is configured to independently emit different spectral profiles of calibration light at different times, each spectral profile of calibration light having one or more peaks at different wavelengths, such that the emitted calibration light is directed along at least a portion of each of the optical paths, wherein the calibration light source is different than the sample illumination source;
   one or more processors; and
   a memory that stores computer-executable instructions that, when executed by the one or more processors, cause the one or more processors to:
   receive the output data from each of the detectors responsive to that detector receiving calibration light from the calibration light source, and
   determine filtering characteristics for the optical filter elements along each optical path by analyzing the output data produced during the emission of at least two different spectral profiles of calibration light by the calibration light source.

2. The system of claim 1, wherein the computer-executable instructions further include instructions that, when executed by the one or more processors, cause the one or more processors to:
   cause the calibration light source to emit, at a first time, first calibration light having a first spectral profile;
   obtain first output data from each of the detectors responsive to the detectors receiving the first calibration light from the calibration light source at the first time;
   cause the calibration light source to emit, at a second time after the first time, second calibration light having the first spectral profile;
   obtain second output data from each of the detectors responsive to the detectors receiving the second calibration light from the calibration light source at the second time; and
   compare the second output data to the first output data to determine if there has been a change in optical performance of the system.

3. The system of claim 1, wherein:
the one or more detectors includes a first detector, and
the computer-executable instructions further include instructions that, when executed by the one or more processors, cause the one or more processors to:
obtain first output data from the first detector produced in response to detection by the first detector of first calibration light having a first spectral profile;
obtain second output data from the first detector produced in response to detection by the first detector of second calibration light having a second spectral profile that is different from the first spectral profile;
compare the first output data and the second output data against a database of spectral fingerprints, each spectral fingerprint associated with a particular filtering characteristic and having a first component associated with the first spectral profile and a second component associated with the second spectral profile; and
determine the filtering characteristics for the optical filter elements along the optical path corresponding to the first detector by identifying the particular filtering characteristic by, at least in part, correlating the first output data and the second output data with the first component and the second component, respectively.

4. The system of claim 1, wherein:
the one or more detectors includes a first detector, and
the computer-executable instructions further include instructions that, when executed by the one or more processors, cause the one or more processors to:
obtain first output data from the first detector produced in response to detection by the first detector of first calibration light having a first spectral profile;
compare the first output data against a database of spectral fingerprints, each spectral fingerprint associated with a particular filtering characteristic and having a first component associated with the first spectral profile; and
determine the filtering characteristics for the optical filter elements along the optical path corresponding to the first detector by identifying the particular filtering characteristic by, at least in part, correlating the first output data with the first component, respectively.

5. The system of claim 1, wherein:
the one or more detectors includes a first detector, and
the computer-executable instructions further include instructions that, when executed by the one or more processors, cause the one or more processors to:
obtain first output data from the first detector produced in response to detection by
the first detector of first calibration light having a first spectral profile;
obtain second output data from the first detector produced in response to detection by the first detector of second calibration light having a second spectral profile that is different from the first spectral profile and that also overlaps with the first spectral profile;
compare the first output data and the second output data by determining a ratio of the second output data to the first output data; and
determine the filtering characteristics for the optical filter elements along the optical path corresponding to the first detector by, at least in part, comparing the ratio against intensity ratios of the first spectral profile and the second spectral profile corresponding with a plurality of wavelengths.

6. The system of claim 5, wherein the computer-executable instructions further include instructions that, when executed by the one or more processors, cause the one or more processors to:
obtain additional output data from the first detector produced in response to detection by the first detector of one or more additional emissions of calibration light having spectral profiles other than the first spectral profile and the second spectral profile; and
determine that none of the additional output data indicates any detection of the additional emissions of calibration light by the first detector.

7. The system of claim 5, wherein the computer-executable instructions further include instructions that, when executed by the one or more processors, cause the one or more processors to:
compare the filtering characteristics for the optical filter elements along the optical path with predefined filtering characteristics associated with that optical path; and
provide an indication via a user interface as to whether the filtering characteristics for the optical filter elements along the optical path are within a threshold amount of the predefined filtering characteristics associated with that optical path.

8. The system of claim 1, wherein a different subset of the one or more optical paths passes through each optical filter element.

9. The system of claim 1, wherein each of the one or more optical paths is defined, at least in part, by an optical fiber, and wherein each optical fiber has an end configured for capturing light emitted from the calibration light source.

10. The system of claim 9, wherein the focusing optics include objective optics configured to focus the sample light onto the ends of the one or more optical fibers.

11. The system of claim 10, wherein the calibration light source comprises a plurality of light emitting diodes (LEDs) configured to illuminate the ends of the one more optical fibers without passing through the focusing optics.

12. The system of claim 11, wherein the plurality of LEDs comprise LEDs having different peak wavelengths, and wherein the calibration light source is configured to emit different spectral profiles of calibration light at different times by separately illuminating the LEDs having different peak wavelengths.

13. The system of claim 12, wherein each of the plurality of LEDs is configured to emit calibration light having a bandwidth in a range of 100 nm to 200 nm.

14. The system of claim 12, wherein each of the plurality of LEDs is configured to emit calibration light having a bandwidth in a range of 10 nm to 100 nm.

15. The system of claim 1, wherein each of the one or more optical paths pass through a pinhole aperture.

16. The system of claim 1, wherein:
the calibration light source includes a printed circuit board having an opening through it and a plurality of light emitting diodes (LEDs) placed around the periphery of the opening,
the plurality of LEDs are configured to emit the calibration light, and
the one or more optical paths pass through the opening.

17. The system of claim 1, wherein the calibration light source is configured to emit calibration light that is directed through the sample location and into the focusing optics, and wherein sample illumination source is oriented such that the light delivered by the sample illumination source to each sample location is directed into each sample location along a direction that is not aligned with the one or more optical paths.

18. A method for determining filtering characteristics for a plurality of optical filter elements in a flow cytometry system, wherein a different subset of a plurality of optical paths passes through each of the optical filter elements, and wherein each optical path directs emitted or scattered sample light from a sample location to a corresponding detector, the method comprising:
emitting different spectral profiles of calibration light from a calibration light source of the flow cytometry system at different times, wherein each spectral profile of calibration light has one or more intensity peaks at different wavelengths, and wherein the calibration light source is different than a sample illumination source of the flow cytometry system, the sample illumination source being configured to deliver light to each of the sample locations, thereby producing the emitted or scattered sample light;
directing some of the calibration light along at least a portion of each of the optical paths;
measuring, for each different spectral profile of calibration light, the light intensity at each of the detectors, wherein each of the detectors produces output data that is indicative of the measured light intensity of the calibration light that reaches the detector; and
analyzing the output data from one of the detectors produced during the emission of at least two different spectral profiles of calibration light by the calibration light source to determine the filtering characteristics of the optical filter elements along the optical path corresponding to that detector.

19. The method of claim 18, further comprising:
causing the calibration light source to emit, at a first time, first calibration light having a first spectral profile;
obtaining first output data from each of the detectors responsive to the detectors receiving the first calibration light from the calibration light source at the first time;
causing the calibration light source to emit, at a second time after the first time, second calibration light having the first spectral profile;
obtaining second output data from each of the detectors responsive to the detectors receiving the second calibration light from the calibration light source at the second time; and
comparing the second output data to the first output data to determine if there has been a change in optical performance of the flow cytometry system.

20. The method of claim 18, further comprising:
obtaining first output data from a first detector of the detectors produced in response to detection by the first detector of first calibration light having a first spectral profile;
obtaining second output data from the first detector produced in response to detection by the first detector of second calibration light having a second spectral profile that is different from the first spectral profile;
comparing the first output data and the second output data against a database of spectral fingerprints, each spectral fingerprint associated with a particular filtering characteristic and having a first component associated with the first spectral profile and a second component associated with the second spectral profile; and
determining the filtering characteristics for the optical filter elements along the optical path corresponding to the first detector by identifying the particular filtering characteristic by, at least in part, correlating the first output data and the second output data with the first component and the second component, respectively.

21. The method of claim 18, further comprising:
obtaining first output data from a first detector of the detectors produced in response to detection by the first detector of first calibration light having a first spectral profile;
comparing the first output data against a database of spectral fingerprints, each spectral fingerprint associated with a particular filtering characteristic and having a first component associated with the first spectral profile; and
determining the filtering characteristics for the optical filter elements along the optical path corresponding to the first detector by identifying the particular filtering characteristic by, at least in part, correlating the first output data with the first component, respectively.

22. The method of claim 18, further comprising:
obtaining first output data from a first detector of the detectors responsive to detection by the first detector of first calibration light having a first spectral profile;
obtaining second output data from the first detector responsive to detection by the first detector of second calibration light having a second spectral profile that is different from the first spectral profile and that also overlaps with the first spectral profile;
comparing the first output data and the second output data by determining a ratio of the second output data to the first output data; and
determining the filtering characteristics for the optical filter elements along the optical path corresponding to the first detector by comparing the ratio against intensity ratios of the first spectral profile and the second spectral profile corresponding with a plurality of wavelengths.

23. The method of claim 22, further comprising:
obtaining additional output data from the first detector responsive to detection by the first detector of one or more additional emissions of calibration light having spectral profiles other than the first spectral profile and the second spectral profile; and
determining that none of the additional output data indicates any detection of the additional emissions of calibration light by the first detector.

24. The method of claim 18, wherein the calibration light source comprises a plurality of light emitting diodes (LEDs) having different peak wavelengths, and wherein emitting different spectral profiles of calibration light at different times comprises separately illuminating different subsets of plurality of LEDs, where in each different subset has a different set of peak wavelengths.

25. The method of claim 18, wherein each optical path is defined, at least in part, by an optical fiber, and wherein directing some of the calibration light along at least a portion of each of the optical paths comprises orienting the calibration light source so that the emitted calibration light illuminates an end of the optical fiber of each optical path with a light magnitude range that is substantially similar to that of the sample light transmitted along each optical path.

26. The method of claim 18, wherein the calibration light source is oriented so that the emitted calibration light is not delivered to the sample location.

* * * * *